(12) United States Patent
Omura et al.

(10) Patent No.: US 7,514,250 B2
(45) Date of Patent: Apr. 7, 2009

(54) COENZYME-BINDING GLUCOSE DEHYDROGENASE

(75) Inventors: Hironori Omura, Hiroshima (JP); Hirokazu Sanada, Hiroshima (JP); Takako Yada, Hiroshima (JP); Tetsunari Morita, Hiroshima (JP); Mika Kuyama, Hiroshima (JP); Tokuji Ikeda, Kyoto (JP); Kenji Kano, Kyoto (JP) j; Seiya Tsujimura, Nara (JP)

(73) Assignee: Ikeda Food Research Co., Ltd., Hiroshima (JP)

( * ) Notice: Subject to any disclaimer, the term of this patent is extended or adjusted under 35 U.S.C. 154(b) by 361 days.

(21) Appl. No.: 10/540,025

(22) PCT Filed: Dec. 24, 2003

(86) PCT No.: PCT/JP03/16603

§ 371 (c)(1),
(2), (4) Date: Oct. 14, 2005

(87) PCT Pub. No.: WO2004/058958

PCT Pub. Date: Jul. 15, 2004

(65) Prior Publication Data

US 2006/0063217 A1     Mar. 23, 2006

(30) Foreign Application Priority Data

Dec. 24, 2002  (JP)  ............... 2002-373297

(51) Int. Cl.
    *C12N 9/02*  (2006.01)
(52) U.S. Cl. .................. 435/189; 435/14; 435/69.1
(58) Field of Classification Search ................. 435/189
    See application file for complete search history.

(56) References Cited

U.S. PATENT DOCUMENTS

| | | | |
|---|---|---|---|
| 6,103,509 A | 8/2000 | Sode | |
| 7,132,270 B2 * | 11/2006 | Kratzsch et al. | ............ 435/190 |

FOREIGN PATENT DOCUMENTS

| | | |
|---|---|---|
| EP | 1 167 519 | 1/2002 |
| EP | 1 176 202 | 1/2002 |
| JP | 10-243786 | 9/1998 |
| JP | 2000-350588 | 12/2000 |
| JP | 2001-197888 | 7/2001 |
| JP | 2001-346587 | 12/2001 |
| JP | 2002-526759 | 8/2002 |
| WO | 02/34919 | 5/2002 |

OTHER PUBLICATIONS

Dickinson et al , The Reactions of 1,0-Phenanthroline with Yeat Alcohol Dehydrogenase, Biochem Journal, 1977, vol. 167, p. 237-244.*

Pire et al , NADP glucose dehydrogenase from Haloferax mediterranei: kinetic mechanism and metal content, Journal fo Molecular Catalysis B:Enzymatic vol. 10, 2000, p. 409-417.*

K. Matsushita et al., "Membrane-bound D-Glucose Dehydrogenase from *Pseudomonas* sp.: Solubilization, Purification and Characterization", Agric. Biol. Chem., vol. 44, No. 7, pp. 1505-1512, 1980.

M. Ameyama et al., "D-Glucose Dehydrogenase of *Gluconobacter suboxydans*: Solubilization, Purification and Characterization", Agric. Biol. Chem., vol. 45, No. 4, pp. 851-861, 1981.

M. Ameyama et al., "Purification and Characterization of the Quinoprotein D-Glucose Dehydrogenase Apoenzyme from *Escherichia coli*", Agric. Biol. Chem., vol. 50, No. 1, pp. 49-57, 1986.

P. Dokter et al., "The in vivo and in vitro substrate specificity of quinoprotein glucose dehydrogenase of *Acinetobacter calcoaceticus* LMD 79.41", FEMS Microbiology Letters, vol. 43, pp. 195-200, 1987.

S. Igarashi et al., "Construction and Characterization of Mutant Water-Soluble PQQ Glucose Dehydrogenases with Altered $K_m$ Values-Site-Directed Mutagenesis Studies on the Putative Active Site", Biochemical and Biophysical Research Communications, vol. 264, pp. 820-824, 1999.

K. Sode et al., "Improved substrate specificity and dynamic range for glucose measurement of *Escherichia coli* PQQ glucose dehydrogenase by site directed mutagenesis", Biotechnology Letters, vol. 19, No. 11, pp. 1073-1077, Nov. 1997.

G. E. Cozier et al., "Characterization of the membrane quinoprotein glucose dehydrogenase from *Escherichia coli* and characterization of a site-directed mutant in which histidine-262 has been changed to tyrosine", Biochem. J., vol. 340, pp. 639-647, 1999.

K. Hayano et al., "Purification and Properties of 3-Ketosucrose-forming Enzyme from the Cells of *Agrobacterium tumefaciens*", The Journal of Biological Chemistry, vol. 242, No. 16, pp. 3665-3672, Aug. 25, 1967.

(Continued)

*Primary Examiner*—Ralph Gitomer
*Assistant Examiner*—Tiffany M Gough
(74) *Attorney, Agent, or Firm*—Wenderoth, Lind & Ponack, L.L.P.

(57) ABSTRACT

The present invention provides a microorganism-derived soluble coenzyme-binding glucose dehydrogenase which catalyzes a reaction for oxidizing glucose in the presence of an electron acceptor, has an activity to maltose as low as 5% or less, and is inhibited by 1,10-phenanthroline. The invention also provides a method for producing the coenzyme-binding glucose dehydrogenase, and a method and a reagent for measuring employing the coenzyme-binding glucose dehydrogenase. According to the invention, the coenzyme-binding glucose dehydrogenase can be applied to an industrial field, and a use becomes possible also in a material production or analysis including a method for measuring or eliminating glucose in a sample using the coenzyme-binding glucose dehydrogenase as well as a method for producing an organic compound. It became also possible to provide a glucose sensor capable of accurately measuring a blood sugar level. Therefore, it became possible to provide an enzyme having a high utility, such as an ability of being used for modifying a material in the fields of pharmaceuticals, clinical studies and food products.

7 Claims, 6 Drawing Sheets

OTHER PUBLICATIONS

W. Tsugawa et al., "Fluorescent measurement of 1,5-anhydro-D-glucitol based on a novel marine bacterial glucose dehydrogenase", Enzyme and Microbial Technology, vol. 22, pp. 269-274, 1998.

S. C. Morrison et al., Characterization of a glucose 3-dehydrogenase from the cultivated mushroom (*Agaricus bisporus*), Appl. Microbiol Biotechnol, vol. 51, pp. 58-64, 1999.

T. Bak, "Studies on Glucose Dehydrogenase of *Aspergillus oryzae* II. Purification and Physical and Chemical Properties", Biochim. Biophys. Acta, vol. 139, pp. 277-293, 1967.

T. Bak, "Studies on Glucose Dehydrogenase of *Aspergillus oryzae* III. General Enzymatic Properties", Biochim. Biophys. Acta, vol. 146, pp. 317-327 1967.

T. Bak, "Studies on Glucose Dehydrogenase of *Aspergillus oryzae* IV. Histidyl Residue as an Active Site", Biochim. Biophys. Acta, vol. 146, pp. 328-335, 1967.

Supplementary European Search Report completed Mar. 23, 2006 in the International (PCT) Application No. EP 03789625.5 of which the present application is the U.S. National Stage.

Oubrie, et al., "Active-site structure of the soluble quinoprotein glucose dehydrogenase complexed with methylhydrazine: A covalent cofactor-inhibitor complex," Proceedings of the National Academy of Sciences of USA, National Academy of Science, Washington, DC, vol. 96, No. 21, Oct. 1999, pp. 11787-11791.

Yoshida H., et al., "Construction of Multi-Chimeric Pyrroloquinoline Quinone Glucose Dehydrogenase with Improved Enzymatic Properties and Application In Glucose Monitoring," Biotechnology Letters, vol. 22, No. 18, Sep. 2000, Abstract.

\* cited by examiner

COENZYME-BINDING GLUCOSE DEHYDROGENASE

This application is a U.S. national stage of International Application No. PCT/JP2003/016603 filed Dec. 24, 2003.

TECHNICAL FIELD

The present invention relates to a novel soluble coenzyme-binding glucose dehydrogenase, a method for producing the coenzyme-binding glucose dehydrogenase, and a microorganism having an ability of producing the coenzyme-binding glucose dehydrogenase.

The invention also relates to a method for measuring glucose in a sample employing the coenzyme-binding glucose dehydrogenase, and a reagent and a reagent composition containing the coenzyme-binding glucose dehydrogenase. Moreover, the invention relates to utilization in producing and analyzing a material such as a starting material, including a method for producing an organic compound.

The invention further relates to a biosensor capable of rapidly and conveniently quantifying a particular component in a sample at a high accuracy. Practically, the invention relates to a glucose sensor employing the coenzyme-binding glucose dehydrogenase.

BACKGROUND ART

Glucose is present in blood and utilized as an important marker for diabetes. A method for measuring a glucose has conventionally been a chemical method or an enzymatic method, and an enzymatic method is regarded generally to be excellent in view of the specificity and the safety. Such an enzymatic method is, for example, be a measurement using a glucose oxidase, glucose-6-phosphate dehydrogenase or an NAD(P)-dependent glucose dehydrogenase. However, the methods employing the glucose oxidase and the glucose-6-phosphate dehydrogenase are not convenient reaction systems since they employ a plural of enzymes. The methods employing the glucose-6-phosphate dehydrogenase and the NAD(P)-dependent glucose dehydrogenase pose a complication due to the requirement of adding a coenzyme NAD(P) to the reaction systems.

Recently, various biosensors were proposed as modes for quantifying a particular component in a sample conveniently without diluting or stirring a sample solution. For example, a biosensor was proposed in which an electrode system consisting of an action electrode, a counter electrode and a reference electrode was formed by a screen printing on an insulating board. This electrode system and the like was in contact with an enzymatic reaction layer formed thereon containing a hydrophilic polymer, a redox enzyme and an electron acceptor.

The number of diabetes patient is increasing year by year, and a method for measuring a blood sugar and a means for controlling the blood sugar level are desired which can be utilized not only in a hospital but also at home and which is convenient. While a simple glucose sensor is employed currently for measuring the blood sugar, it frequently employs a glucose oxidase which is highly suspected to give a measured value involving an error due to a level of the residual oxygen. On the other hand, a biosensor employing a glucose dehydrogenase which is dependent on a nicotinamide-based coenzyme exhibits a high background noise and involves a complicated reaction system due to the requirement of adding a coenzyme or an auxiliary enzyme separately, and it also suffers from a disadvantage due to the requirement of an expensive optical system upon measuring a chromogenic system.

As an enzyme which is not affected by the residual oxygen level and which can act on glucose in the absence of NAD(P), a glucose dehydrogenase whose coenzyme is pyrroloquinolinequinone is known, but the pyrroloquinolinequinone problematically tends to dissociate from the enzyme. A glucose dehydrogenase whose coenzyme is pyrroloquinolinequinone disclosed in JP-A-2000-350588 and JP-A-2001-197888 has a disadvantageously low selectivity for glucose. On the other hand, a glucose dehydrogenase whose coenzyme is the pyrroloquinolinequinone derived from *Escherichia coli* (JP-A-10-243786), a glucose dehydrogenase whose coenzyme is the pyrroloquinolinequinone derived from *Pseudomonas* sp. (Agric. Biol. Chem. (1980) 44:1505-1512) and a glucose dehydrogenase whose coenzyme is the pyrroloquinolinequinone derived from Gluconobacter suboxydans (Agric. Biol. Chem. (1981) 45:851-861) had the respective activity on maltose of 3%, 3.2% and 5%, but were accompanied with the complication due to the requirement of a solubilization and an extraction of the enzymes since they were existing in a membrane fraction of the bacterial bodies.

The coenzyme-binding glucose dehydrogenases which oxidize a hydroxyl group in the 3rd-position of glucose were also reported in J. Biol. Chem. (1967) 242: 3665-3672, Appl. Microbiol. Biotechnol. (1999) 51: 58-64, Appl. Biochem. Biotechnol. (1996) 56: 301-310 and Enzyme Microb. Technol. (1998) 22:269-274, but any of them exhibits a poor selectivity for glucose. Since maltose is employed widely as an infusion component and the blood maltose level in an infused patient is high, it is desired to develop an enzyme for measuring the blood sugar which is capable of acting specifically on glucose and has low activity especially on maltose.

In order to respond the industrial needs mentioned above, an objective of the invention is to provide a novel glucose dehydrogenase which exhibits an excellent substrate-recognizing ability toward glucose and which has low activity on maltose, and also to provide a method for producing the same and a microorganism having an ability of producing the same.

Another objective of the invention is to provide excellent glucose measuring method, measuring reagent and biosensor which employ the novel glucose dehydrogenase and which are capable of quantifying glucose rapidly and conveniently at a high accuracy, as well as a glucose-eliminating reagent.

DISCLOSURE OF THE INVENTION

The invention is accomplished for solving the problems mentioned above, and the inventors made an effort in various ways and then focused on a novel soluble coenzyme-binding glucose dehydrogenase. The coenzyme-binding glucose dehydrogenase catalyzes a glucose-oxidizing reaction in the presence of an electron acceptor, and is classified for example as EC (Enzyme Code) 1.1.99. The inventors also made an effort in characterizing various microorganisms producing the coenzyme-binding glucose dehydrogenase, and finally discovered a coenzyme-binding glucose dehydrogenase-producing microorganism and a coenzyme-binding glucose dehydrogenase.

The invention provides a glucose dehydrogenase to which a coenzyme is bound continuously upon a catalytic reaction. The coenzyme-binding glucose dehydrogenase has a physicochemical ability of catalyzing a reaction for oxidizing glucose, especially a hydroxyl group in the 1st-position of glucose, in the presence of an electron acceptor. The coenzyme-binding glucose dehydrogenase has 5% or less activity to maltose, preferably 3% or less; thus it has a poor activity on the maltose. On the other hand, the coenzyme-binding glucose dehydrogenase allows its enzymatic activity to be inhibited characteristically by 50% or more at 5 mM of 1,10-phenanthroline, preferably by 50% or more at 2 mM as a final concentration of 1,10-phenanthroline, more preferably by 50% or more at 1 mM of 1,10-phenanthroline. The coenzyme-binding glucose dehydrogenase preserves its residual enzymatic activity at a level as high as 85% or more even after a heat treatment for 15 minutes at 50° C. in the presence of 50 mM sodium citrate buffer solution (pH5.5). The coenzyme which is bound to the inventive glucose dehydrogenase may for example be a flavin compound, including a coenzyme such as flavin adenine dinucleotide. The invention also includes, with respect to a protein having the characteristics of those of the coenzyme-binding glucose dehydrogenase and/or characteristics equivalent substantially thereto as well as its salt, a protein which has an amino acid sequence encoding the protein or an amino acid sequence containing a mutation resulting from a deletion, substitution or addition of one or more amino acid residues in the sequence and which is biologically active and stable. Moreover, the inventive coenzyme-binding glucose dehydrogenase is a microorganism-derived coenzyme-binding glucose dehydrogenase, preferably a eukaryotic microorganism-derived coenzyme-binding glucose dehydrogenase, more preferably the deposited strain FERM BP-08578-derived coenzyme-binding glucose dehydrogenase.

It has already been observed that a glucose dehydrogenase whose coenzyme is a flavin adenine dinucleotide exists in a cytoplasm fraction and a culture of *Aspergillus oryzae* (TCHAN-GI BAK (BIOCHEMICA ET BIOPHYSICA ACTA. (1967) 139:277-293)). However, this glucose dehydrogenase is inhibited only by a heavy metal ion, and characterized physicochemically in that it is not inhibited by a metal chelator including 1,10-phenanthroline. Accordingly, in a measurement system employing this glucose dehydrogenase, only a heavy metal can be used as a quencher, which poses a problem associated with a complicated heavy metal waste disposal after completion of the reaction. In addition, this enzyme has a poor stability, and is problematic when used practically. On the other hand, the coenzyme-binding glucose dehydrogenase discovered in this invention is characterized by its higher stability when compared with that of the known *Aspergillus oryzae*-derived coenzyme-binding glucose dehydrogenase, and also by a favorably convenient handling for quenching because of its ability of being inhibited by a trace amount of 1,10-phenanthroline in addition to a heavy metal ion.

The invention provides a method for producing the novel soluble coenzyme-binding glucose dehydrogenase.

The invention provides a microorganism having an ability of producing the novel soluble coenzyme-binding glucose dehydrogenase. The microorganism is preferably a eukaryotic microorganism, more preferably, genus *Aspergillus*, further preferably, *Aspergillus terreus*, and most preferably, the deposited strain FERM BP-08578.

The invention provides a method using the novel soluble coenzyme-binding glucose dehydrogenase. Preferably, a method for measuring glucose using the coenzyme-binding glucose dehydrogenase is provided for measuring glucose in a sample. A method for eliminating glucose using the coenzyme-binding glucose dehydrogenase and a method for producing an organic compound are also provided.

The invention provides a reagent containing the novel soluble coenzyme-binding glucose dehydrogenase. The reagent is preferably a glucose-measuring reagent containing the coenzyme-binding glucose dehydrogenase employed for measuring the glucose in a sample, and a glucose-eliminating reagent containing the coenzyme-binding glucose dehydrogenase as well as an organic compound-producing reagent.

The invention provides a reagent composition containing the novel soluble coenzyme-binding glucose dehydrogenase. The composition is preferably a glucose-measuring composition containing the coenzyme-binding glucose dehydrogenase employed for measuring glucose in a sample, and a glucose-eliminating composition containing the coenzyme-binding glucose dehydrogenase as well as an organic compound-producing composition.

The invention provides a biosensor employing the novel soluble coenzyme-binding glucose dehydrogenase and a biosensor capable of quantifying and/or qualifying a particular component in a sample. Such a biosensor is preferably a glucose sensor employing the coenzyme-binding glucose dehydrogenase.

One preferred embodiment of these inventive measurement methods, measurement reagents, measurement compounds and biosensors is characterized by the use of potassium ferricyanide (potassium hexacyanoferrate (III)) at a final concentration of 2 mM to 500 mM.

In the invention, a value of percentage (%) represents "substrate specificity". For example, in the expressions "activity to maltose", "activity" toward maltose" or an analogous expression, according to the coenzyme-binding glucose dehydrogenase, such a value also represents for a percentage of a relative intensity of an enzymatic activity on the maltose or other action targets based on the enzymatic activity on glucose being regarded as 100%.

BEST MODE FOR CARRYING OUT THE INVENTION

Figure 1:
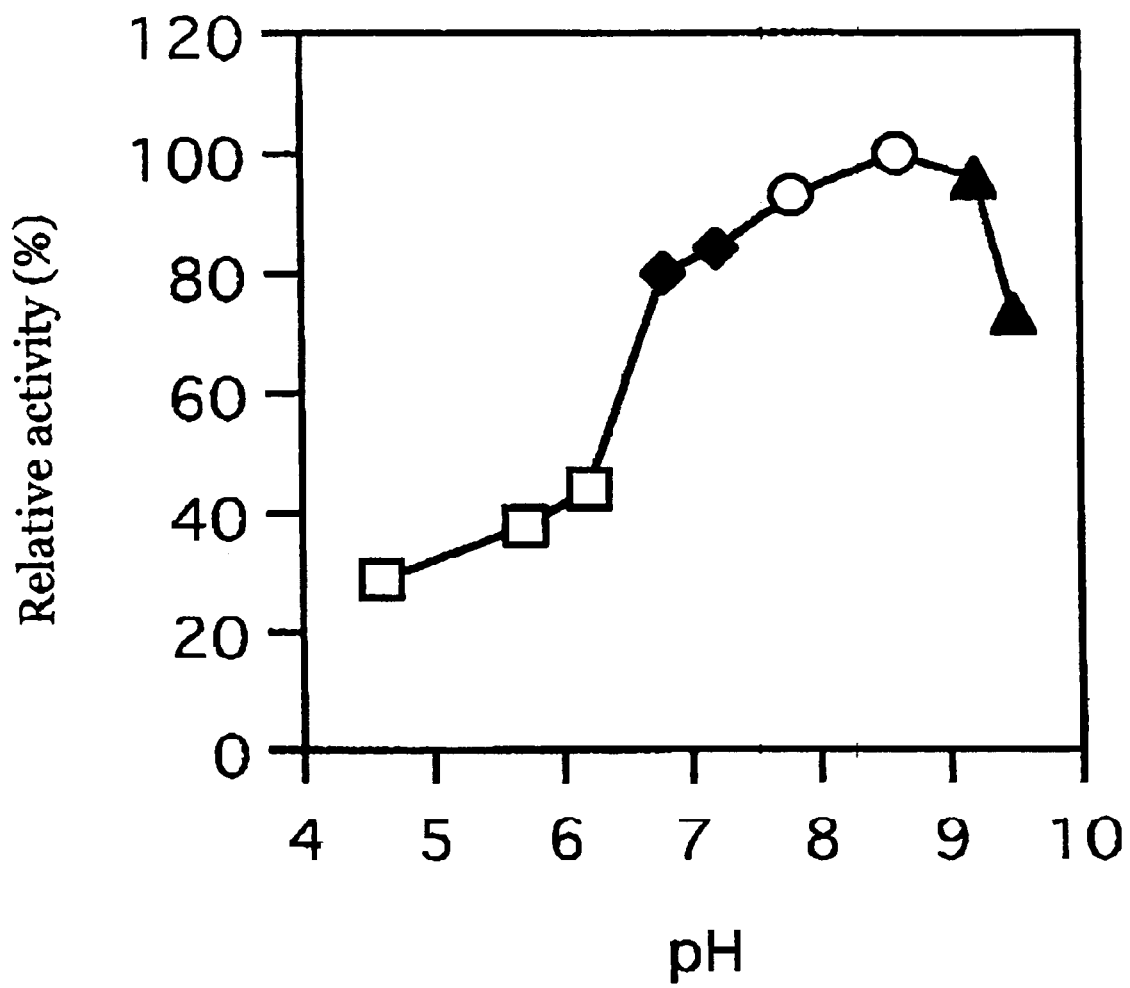
FIG. 1 shows a graph representing the relationship between the relative activity (%) of the coenzyme-binding glucose dehydrogenase and the pH, in Example 3 (3.2). Symbols show measured values and types of buffer solutions, which are □: citric acid-sodium phosphate buffer (pH4.6 to 6.2), ♦: potassium phosphate buffer (pH6.8 to 7.2), ○: Tris-HCl buffer (pH7.8 to 8.6) and ▲: glycine-sodium hydroxide (pH9.2 to 9.5). The optimum pH of the enzyme was 7.0 to 9.0.

An inventive coenzyme-binding glucose dehydrogenase may for example be an enzyme classified as EC 1.1.99, preferably EC 1.1.99.10, EC 1.1.99.13 or EC 1.1.99.17, and is a coenzyme-binding enzyme, preferably a soluble coenzyme-binding enzyme. That is, it is an enzyme capable of being obtained in the state of an aqueous solution without using any surfactant in a step of extraction/purification of the enzyme. As used herein, a coenzyme may be any flavin compound, such as flavin adenine dinucleotide, flavin mononucleotide and the like.

The inventive coenzyme-binding glucose dehydrogenase may be a glucose dehydrogenase to which a coenzyme is bound always over the period of the catalytic reaction. The coenzyme-binding glucose dehydrogenase has at least the following characteristics; that is a physicochemical property for catalyzing a reaction for oxidizing glucose in the presence of an electron acceptor, especially for catalyzing a reaction for oxidizing a hydroxyl group in the 1st-position of the glucose. In addition, the coenzyme-binding glucose dehydrogenase has a low activity on maltose, which is at a level for example of 5% or below, preferably 3% or below. Moreover, the enzymatic activity of the coenzyme-binding glucose dehydrogenase is inhibited by 50% or more at 5 mM of 1,10-phenanthroline, preferably by 50% or more at 2 mM as a final concentration of 1,10-phenanthroline, more preferably by 50% or more at 1 mM of 1,10-phenanthroline, especially by 60% or more at 1 mM of 1,10-phenanthroline. The coenzyme-binding glucose dehydrogenase preserves its residual enzymatic activity at a level as high as 85% or more even after a heat treatment for 15 minutes at 50° C. in the presence of 50 mM sodium citrate buffer solution (pH5.5). Moreover, the invention relates to coenzyme-binding glucose dehydrogenase having the physicochemical characteristics described above; or an amino acid sequence encoding the physicochemical characteristics, wherein the amino acid sequence is a protein or a salt as follows: the amino acid sequence encoding the protein or the salt contains a mutation resulting from a deletion, substitution or addition of one or more amino acid residues in the sequence, and such the resultant protein and the salt are biologically active and stable, with respect to the protein or its salt having the activity substantially equivalent to that of the coenzyme-binding glucose dehydrogenase.

The protein or its salt, which are the inventive coenzyme-binding glucose dehydrogenase, is preferably one derived from a microorganism having the physicochemical characteristics described above. A microorganism from which the inventive coenzyme-binding glucose dehydrogenase is derived and a microorganism having an ability of producing the inventive coenzyme-binding glucose dehydrogenase may for example be those classified into prokaryotic microorganisms such as genus *Archangium*, genus *Arcaeoglobus*, genus *Arsenophonus*, genus *Ahrensia*, genus *Aureobacterium*, genus *Aerococcus*, genus *Aeropyrum*, genus *Aeromicrobium*, genus *Aeromonas*, genus *Aquifex*, genus *Aquaspirillum*, genus *Aquabacter*, genus *Aquabacterium*, genus *Aquamicrobium*, genus *Actinolloteichus*, genus *Actinokineospora*, genus *Actinocorallia*, genus *Actinosynnema*, genus *Actinosporangium*, genus *Actinobaculum*, genus *Actinobacilus*, genus *Actinopycnidium*, genus *Actinobispora*, genus *Actinoplanes*, genus *Actinopolyspora*, genus *Actinopolymorpha*, genus *Actinomyces*, genus *Actinomadura*, genus *Acrocarpospora*, genus *Agrococcus*, genus *Agrobacterium*, genus *Agromyces*, genus *Agromatium*, genus *Agromonas*, genus *Achromobacter*, genus *Acholeplasma*, genus *Asaia*, genus *Acidianus*, genus *Acidispaera*, genus *Acidiphilium*, genus *Acidimicrobium*, genus *Acidilobus*, genus *Acidaminococcus*, genus *Acidaminobacter*, genus *Acidithiobacillus*, genus *Agitococcus*, genus *Acidothermus*, genus *Acidocella*, genus *Acidobacterium*, genus *Acidovorax*, genus *Acidomonas*, genus *Acinetobacter*, genus *Asiticcacaulis*, genus *Asteroleplasma*, genus *Acetitomaculum*, genus *Acetivibrio*, genus *Acetoanaerobium*, genus *Acetogenium*, genus *Acetothermus*, genus *Acetonema*, genus *Acetobacter*, genus *Acetobacterium*, genus *Acetohalobium*, genus *Acetofilamentum*, genus *Acetomicrobium*, genus *Azoarcus*, genus *Azospira*, genus *Azospirillum*, genus *Azotobacter*, genus *Azonexus*, genus *Azovibrio*, genus *Azomonas*, genus *Azomonotrichon*, genus *Azorhizobium*, genus *Azorhizophilus*, genus *Atopobacter*, genus *Atopobium*, genus *Anaplasma*, genus *Aneurinibacillus*, genus *Anaeroarcus*, genus *Anaerococcus*, genus *Anaerosinus*, genus *Anaerobacter*, genus *Anaerobaculum*, genus *Anaerobispirillum*, genus *Anaerovibrio*, genus *Anaerofilum*, genus *Anaeroplasma*, genus *Anaerobranca*, genus *Anaerovorax*, genus *Anaeromusa*, genus *Anaerorhabdus*, genus *Anoxybacillus*, genus *Abiotrophia*, genus *Afipia*, genus *Amaricoccus*, genus *Amycolata*, genus *Amycolatopsis*, genus *Aminobacter*, genus *Aminobacterium*, genus *Aminomonas*, genus *Amoebobacter*, genus *Ammoniphilus*, genus *Ammonifex*, genus *Amorphosporangium*, genus *Arachnia*, genus *Alysiella*, genus *Alicyclobacillus*, genus *Alishewanella*, genus *Alcanivorax*, genus *Arcanobacterium*, genus *Alcaligenes*, genus *Alkalibacterium*, genus *Alkaliphilus*, genus *Arcobacter*, genus *Arthrobacter*, genus *Alterococcus*, genus *Alteromonas*, genus *Albibacter*, genus *Alloiococcus*, genus *Allochromatium*, genus *Arhodomonas*, genus *Allomonas*, genus *Allorhizobium*, genus *Anacalochloris*, genus *Anacalomicrobium*, genus *Angiococcus*, genus *Angulomicrobium*, genus *Ancylobacter*, genus *Antarctobacter*, genus *Amphibacillus*, genus *Ampullariella*, genus *Ignavigranum*, genus *Idiomarina*, genus *Isochromatium*, genus *Isosphaera*, genus *Ideonella*, genus *Ilyobacter*, genus *Intrasporagium*, genus *Weeksella*, genus *Wigglesworthia*, genus *Williamsia*, genus *Wolinella*, genus *wolbachia*, genus *Ureplasma*, genus *Ureibacillus, Eikenella*, genus *Ehrlichia*, genus *Exiguobacterium*, genus *Excellospora*, genus *Ectothiorhodospira*, genus *Aegyptianella*, genus *Eggerthella*, genus *Escherichia*, genus *Edwardsiella*, genus *Ewingella*, genus *Eperythrozonn*, genus *Erysipelothrix*, genus *Erythrobacter*, genus *Erythromicrobium*, genus *Erythromonas*, genus *Elytrosporangium*, genus *Yersinia*, genus *Erwinia*, genus *Eremococcus*, genus *Ensifer*, genus *Enterococcus*, genus *Enterobacter*, genus *Entomoplasma*, genus *Enhydrobacter*, genus *Empedobacter, Oenococcus*, genus *Oerskovia*, genus *Oceanimonas*, genus *Oceanospirillum*, genus *Oxalobacater*, genus *Oxalophagus*, genus *Oxobacter*, genus *Octadecabacter*, genus *Ochrobactrum*, genus *Oscillochloris*, genus *Oscillospira*, genus *Obesumbacterium*, genus *Orientia*, genus *Oligella*, genus *Oligotropha*, genus *Oribaculum*, genus *Ornithinicoccus*, genus *Ornithinimicrobium*, genus *Ornithobacterium*, genus *Orenia*, genus *Gardnerella*, genus *Carnimonas*, genus *Carnobacterium*, genus *Couchioplanes*, genus *Cowdria*, genus *Caulobacter*, genus *Caseobacter*, genus *Catenibacterium*, genus *Catenuloplanes*, genus *Catenococcus*, genus *Catellatospora*, genus *Catonella*, genus *Capsularis*, genus *Capnocytophaga*, genus *Gallionella*, genus *Carvophanon*, genus *Gallicola*, genus *Calymmatobacterium*, genus *Cardiobacterium*, genus *Caldicellulosiruptor*, genus *Caldivirga*, genus *Calderobacterium*, genus *Carboxydibrachium*, genus *Carboxydothermus*, genus *Carbophilus*, genus *Caloramator*, genus *Xanthobacter, Xanthomonas*, genus *Xylella*, genus *Xylophilus*, genus *Xenorhabdus*, genus *Kitasatoa*, genus

*Kirasatospora*, genus *Chitinophaga*, genus *Kytococcus*, genus *Kineococcus*, genus *Kineosporia*, genus *Quinella*, genus *Kibdelosporangium*, genus *Campylobacter*, genus *Kingella*, genus *Kutzneria*, genus *Cupriavidus*, genus *Craurococcus*, genus *Glaciecola*, genus *Gracilibacillus*, genus *Granulicatella*, genus *Grahamella*, genus *Clavibacter*, genus *Chlamydia*, genus *Chlamydophila*, genus *Cryobacterium*, genus *Glycomyces*, genus *Chrysiogenes*, genus *Cristispira*, genus *Chryseobacterium*, genus *Chryseomonas*, genus *Crinalium*, genus *Cryptosporangium*, genus *Cryprobacterium*, genus *Kluyvera*, genus *Kribbella*, genus *Gluconacetobacter*, genus *Gluconobacter*, genus *Kurthia*, genus *Curtobacterium*, genus *Crenothrix*, genus *Klebsiella*, genus *Clevelandina*, genus *Crossiella*, genus *Clostridium*, genus *Clobicatella*, genus *CHromatium*, genus *Chromobacterium*, genus *Chromohalobacter*, genus *Chloronema*, genus *Chrorobium*, genus *Chloroflexus*, genus *Chloroherpeton*, genus *Caedibacter*, genus *Ketogulonicigenium*, genus *Gemmata*, genus *Gemmiger*, genus *Gemella*, genus *Gemmobacter*, genus *Chelatococcus*, genus *Chelatobacter*, genus *Gelidibacter*, genus *Coenonia*, genus *Coxiella*, genus *Kocuria*, genus *Koserella*, genus *Coprococcus*, genus *Coprothermobacter*, genus *Coprobacillus*, genus *Comamonas*, genus *Coriobacterium*, genus *Corynebacterium*, genus *Collinsella*, genus *Colwellia*, genus *Gordonia*, genus *Conglomeromonas*, genus *Chondromyces*, genus *Thermaerobacter*, genus *Thermus*, genus *Thermacetogenium*, genus *Thermanaerovibrio*, genus *Thermicanus*, genus *Thermithiobacillus*, genus *Thermoactinomyces*, genus *Thermoanaerobacter*, genus *Thermoanaerobacterium*, genus *Thermoanaerobium*, genus *Thermocladium*, genus *Thermocrispum*, genus *Thermocrinis*, genus *Thermochromatium*, genus *Thermococcus*, genus *Thermosipho*, genus *Thermosyntropha*, genus *Thermosphaera*, genus *Thermothrix*, genus *Thermodesulfobacterium*, genus *Thermodesulfovibrio*, genus *Thermodesulforbabdus*, genus *Thermoterrabacterium*, genus *Thermotoga*, genus *Thermonema*, genus *Thermohydrogenium*, genus *Thermobacteroides*, genus *Thermobacillus*, genus *Thermohalobacter*, genus *Thermobispora*, genus *Thermobifida*, genus *Thermofilum*, genus *Thermobranchium*, genus *Thermoplasma*, genus *Thermoproteus*, genus *Thermomicrobium*, genus *Thermomonospora*, genus *Thermoleophilum*, genus *Cytophaga*, genus *Zymobacter*, genus *Zymophilus*, genus *Zymomonas*, genus *Sagittula*, genus *Saccharococcus*, genus *Saccharothrix*, genus *Saccharobacter*, genus *Saccharopolyspora*, genus *Saccharomonospora*, genus *Zavarzinia*, genus *Subtercola*, genus *Saprospira*, genus *Samsonia*, genus *Salinicoccus*, genus *Salinvibrio*, genus *Salibacillus*, genus *Sarcobium*, genus *Sarcina*, genus *Salmonella*, genus *Salegentibacter*, genus *Sanguibacter*, genus *Sandaracinobater*, genus *Dyadobacter*, genus *Dialister*, genus *Dietzia*, genus *Shewanella*, genus *Geothrix*, genus *Geodermatophilus*, genus *Geotoga*, genus *Geobacter*, genus *Geobacillus*, genus *Geovibrio*, genus *Dictyoglomus*, genus *Cycloclasticus*, genus *Psychroserpens*, genus *Psychrobacter*, genus *Cyclobacterium*, genus *Psychroflexus*, genus *Psychromonas*, genus *Sigella*, genus *Dichelobacter*, genus *Dichoromicrobium*, genus *Dysgonomonas*, genus *Cystobacter*, genus *Citrobacter*, genus *Synergistes*, genus *Sinorhizobium*, genus *Diplocalyx*, genus *Simkania*, genus *Simonsiella*, genus *Janibacter*, genus *Janthinobacterium*, genus *Pseudaminobacter*, genus *Pseudoamyclata*, genus *Pseudoalteromonas*, genus *Pseudoxanthomonas*, genus *Pseudocaedibacter*, genus *Pseudonocardia*, genus *Pseudobutyrivibrio*, genus *Pseudomonas*, genus *Pseudoramibacter*, genus *Schwartzia*, genus *Jonesia*, genus *Johnsonella*, genus *Silicibacter*, genus *Syntrophus*, genus *Syntrophococcus*, genus *Syntrophothermus*, genus *Syntrophospora*, genus *Syntrophobacter*, genus *Syntrophobotulus*, genus *Syntrophomonas*, genus *Symbiotes*, genus *Symbiobacterium*, genus *Zoogloea*, genus *Duganella*, genus *Schineria*, genus *Succiniclasticum*, genus *Succinispira*, genus *Succinivibrio*, genus *Succinimnonas*, genus *Skermania*, genus *Skermanella*, genus *Starkeya*, genus *Stappia*, genus *Staphylococcus*, genus *Staphylothermus*, genus *Staleya*, genus *Stygiolobus*, genus *Stibiobacter*, genus *Stigmatella*, genus *Stetteria*, genus *Stenotrophomonas*, genus *Stella*, genus *Suttrella*, genus *Suttonella*, genus *Stomatococcuus*, genus *Streptoalloteichus*, genus *Streptococcus*, genus *Streptosporangium*, genus *Streptoverticillium*, genus *Streptobacillus*, genus *Streptomyces*, genus *Streptomonospora*, genus *Spirillum*, genus *Spirilliplanes*, genus *Spirillospora*, genus *Spirosoma*, genus *Spiroplasma*, genus *Spirochaeta*, genus *Sphingobacterium*, genus *Sphingobium*, genus *Sphingopyxis*, genus *Sphaerotilus*, genus *Spaerobacter*, genus *Sphingomonas*, genus *Sporichthya*, genus *Sporocytophaga*, genus *Sporosarcina*, genus *Sporotomaculum*, genus *Sporobacter*, genus *Sporobacterium*, genus *Sporohalobacter*, genus *Sporomusa*, genus *Sporolactobacillus*, genus *Smithella*, genus *Slackia*, genus *Sulfitobacter*, genus *Sulfobacillus*, genus *Sulfophobococcus*, genus *Sulfolobus*, genus *Sulfurisphaera*, genus *Sulfurococcus*, genus *Sulforospirillum*, genus *Cedecea*, genus *Setobacterium*, genus *Sebaldella*, genus *Serratia*, genus *Seliberia*, genus *Cellvibrio*, genus *Cerpula*, genus *Serpulina*, genus *Serpens*, genus *Cellulosimicrobium*, genus *Cellulophaga*, genus *Cellulomonas*, genus *Selenihalanaerobacter*, genus *Selenomonas*, genus *Centipeda*, genus *Sodalis*, genus *Zobellia*, genus *Sporobacterium*, genus *Thauera*, genus *Dactylosporangium*, genus *Tatumella*, genus *Tatlockia*, genus *Thalassomonas*, genus *Thialkalicoccus*, genus *Thialkalivibrio*, genus *Thialkalimicrobium*, genus *Thiocapsa*, genus *Thiococcus*, genus *Thiodictyon*, genus *Thiocystis*, genus *Thiospira*, genus *Thiospirillum*, genus *Thiosphaera*, genus *Thiothrix*, genus *Thiobacterium*, genus *Thiobacillus*, genus *Thiohalocapsa*, genus *Thioflavicoccus*, genus *Thiovulum*, genus *THioploca*, genus *THiopedia*, genus *Thiomargarita*, genus *Thiomicrospira*, genus *Thiomonas*, genus *Thiolamprovum*, genus *Thiorhodococcus*, genus *THiorhodospira*, genus *Thiorhodovibrio*, genus *Tissierella*, genus *Chania*, genus *Tindallia*, genus *Tsukamurella*, genus *Turicella*, genus *Deinococcus*, genus *Deinobacter*, genus *Taylorella*, genus *Tectibacter*, genus *Dechlorosoma*, genus *Dechloromonas*, genus *Tessaracoccus*, genus *Desulfacinum*, genus *Desulfitobacterium*, genus *Desulfocapsa*, genus *Desulfococcus*, genus *Desulfosarcina*, genus *Desulfospira*, genus *Desulfosporosinus*, genus *Desulfocella*, genus *Desulfotalea*, genus *Desulfotignum*, genus *Desulfotomaculum*, genus *Desulfonatronum*, genus *Desulfonatronovibrio*, genus *Desulfonispora*, genus *Desulfonema*, genus *Desulfovirga*, genus *Desufobacter*, genus *Desulfobacterium*, genus *Desulfobacula*, genus *Desulfobacca*, genus *Desulfobulbus*, genus *Desulfohalobium*, genus *Desulfovibrio*, genus *Desulfofustis*, genus *Desulfofaba*, genus *Desulfofrigus*, genus *Desulfomicrobium*, genus *Desulfomonas*, genus *Desulfomonile*, genus *Desulforhabdus*, genus *Desulforhopalus*, genus *Desulfurella*, genus *Desulfurococcus*, genus *Desulfurobacterium*, genus *Desulfuromusa*, genus *Desulfuromonas*, genus *Desulfurolobus*, genus *Desemzia*, genus *Dethiosulfovibrio*, genus *Tetragenococcus*, genus *Tetrasphaera*, genus *Denitrobacterium*, genus *Denitrovibrio*, genus *Dehalobacter*, genus *Tepidimonas*, genus *Deferribacter*, genus *Defluvibacter*, genus *Devosia*, genus *Demetria*, genus *Terracoccus*, genus *Terrabacter*, genus *Derxia*, genus *Delftia*, genus *Dermacoccus*, genus *Dermatophilus*, genus *Dermabacter*, genus *Telluria*, genus *Deleya*, genus *Dendrosporobacter*, genus *Toxo*- thrix, genus Trabulsiella, genus Trichlorobacter, genus trichococcus, genus Tlumonas, genus Treponema, genus Dolosigranulum, genus Dolosicoccus, genus Tropheryma, genus Neisseria, genus Natrialba, genus Natrinema, genus Natroniella, genus Natronincola, genus Natronococcus, genus Natronobacterium, genus Natronomonas, genus NAtronorubrum, genus Nannocystis, genus Nitrococcus, genus Nitrospina, genus Nitrospira, genus Nitrosococcus, genus Nitrosospira, genus Nitrosomonas, genus Nitorosolobus, genus Nitrobacter, genus Neochlamydia, genus Neorickettsia, genus Nesterenkonia, genus Nevskia, genus Neptunomonas, genus Nocardia, genus Nocardioides, genus Nocardiopsis, genus Nonomuraea, genus Novosphingobium, genus Virgibacillus, genus Hydrogenobacter, genus Hydrogenovibrio, genus Hydrogenophaga, genus Hydrogenophilus, genus Hyperthermus, genus Hyphomicrobium, genus Hyphomonas, genus Paucinonas, genus Bacterionema, genus Bacteriovorax, genus Bacteroides, genus Bactoderma, genus Vagococcus, genus Pasteuria, genus Pasteurella, genus Bacillus, genus Papillibacter, genus Hafnia, genus Hahella, genus Paracraurococcus, genus Parachlamydia, genus Paracoccus, genus Halanaerobacter, genus Halanaerobium, genus Paralactobacillus, genus Variovorax, genus Haliscomenobacter, genus Bartonella, genus Balneatrix, genus Palaeococcus, genus Hallella, genus Haloarcula, genus Haloincola, genus Halochromatium, genus Halococcus, genus Halothermothrix, genus Halogeometricum, genus Halospirulina, genus Halocella, genus Halothiobacillus, genus Haloterrigena, genus Halonatronum, genus Halobaculum, genus Halobacterium, genus Halobacteroides, genus Halobacillus, genus Halobvibrio, genus Haloferax, genus Halomethanococcus, genus Halomonas, genus Halorhabdus, genus Halorubrum, genus Halorubrobacterium, genus Halorhodospira, genus Pantoea, genus Pandoraea, genus Vampirovibrio, genus Picrophilus, genus Piscirickettsia, genus Hippea, genus Vitreoscilla, genus Bifidobacterium, genus Vibrio, genus Hymenobacter, genus Pimelobacter, genus Pilimelia, genus Hirschia, genus Pirella, genus Pirellula, genus Pyrococcus, genus Pyrodictium, genus Pillotina, genus Pyrobaculum, genus Bilophila, genus Pyrolobus, genus Faenia, genus Facklamia, genus Phascolarctobacterium, genus Falcivibrio, genus Fundibacter, genus Finegoldia, genus Fibrobacter, genus Filibacter, genus Filifactor, genus Phyllobacterium, genus Filobacillus, genus Filomicrobium, genus Phaeospirillum, genus Phenylobacterium, genus Ferriacterium, genus Ferrimonas, genus Fervidobacterium, genus Ferroglobus, genus Ferroplasma, genus Phocoenobacter, genus Photobactrium, genus Photorhabdus, genus Formivibrio, genus Fusobacterium, genus Buttiauxella, genus Butyrivibrio, genus Bdellovibrio, genus Budvicia, genus Phennigia, genus Buchnera, genus Fusibacter, genus Prauserella, genus Pragia, genus Bracyspira, genus Bracybacterium, genus Bracymonas, genus Blastochloris, genus Blastococcus, genus Blastobacter, genus Blastomonas, genus Blattabacterium, genus Bradyrhizobium, genus Frateuria, genus Branhamella, genus Planococcus, genus Planotetraspora, genus Planobispora, genus Planopolyspora, genus Planomicrobium, genus Planomonospora, genus Flavimonas, genus Flavobacterium, genus Flammeovirga, genus Frankia, genus Planctomyces, genus Francisella, genus Friedmanniella, genus Frigoribacterium, genus Fluoribacter, genus Burkholderia, genus Brucella, genus Bulleidia, genus Flexistipes, genus Flexithrix, genus Flexibacter, genus Flectobacillus, genus Plesiomonas, genus Brenneria, genus Brevundimonas, genus Brevinema, genus Brevibacterium, genus Brevibacillus, genus Prevotella, genus Prochlorococcus, genus Prochlorothrix, genus Prochloron, genus Brochothrix, genus Prosthecochloris, genus Prosthecobacter, genus Prosthecomicrobium, genus Proteus, genus Protomonas, genus Propionigenium, genus Propionispira, genus Propionispora, genus Propionibacter, genus Propionibacterium, genus Propionivibrio, genus Propioniferax, genus Providencia, genus Promicromonospora, genus Prolinoborus, genus Beijejrinckia, genus Veillonella, genus Beutenbergia, genus Beggiatoa, genus Pectinatus, genus Pectobacterium, genus Pediococcus, genus Pedobacter, genus Pedomicrobium, genus Petrotoga, genus Paenibacillus, genus Beneckea, genus Peptococcus, genus Peptostreptococcus, genus Peptoniphilus, genus Haemobartonella, genus Haemophilus, genus Heliothrix, genus HEliobacterium, genus Heliobacillus, genus HEliophilum, genus Heliorestis, genus Helicobacter, genus Pelistega, genus Pelczaria, genus Bergeyella, genus Helcococcus, genus Verrucosispora, genus Verrucomicrobium, genus Persicobacter, genus Herbaspirillum, genus Herbidospora, genus Herpetosiphon, genus Pelodictyon, genus Pelospora, genus Pelobacter, genus Vogesella, genus Bogoriella, genus Bosea, genus Polaribacter, genus Polaromonas, genus Hollandina, genus Polyangium, genus Polynucleobacter, genus Volcaniella, genus Bordetella, genus Holdemania, genus Porphyrobacter, genus Porphyromonas, genus Borrelia, genus Holospora, genus Holophaga, genus Hongia, genus Meiothermus, genus Mycobacterium, genus Mycoplasma, genus Mycoplana, genus Mycetocola, genus Myroides, genus Magnetospirillum, genus Macrococcus, genus Macromonas, genus Massilia, genus Maricaulis, genus Marichromatium, genus Marinococcus, genus Marinitoga, genus Marinilabilia, genus Marinospirillum, genus Marinobacter, genus Marinobacterium, genus Marinomonas, genus Marmoricola, genus Malonomonas, genus Mannheimia, genus Micavibrio, genus Myxococcus, genus Microellobosporia, genus Micrococcus, genus Microcyclus, genus Microcystis, genus Microscilla, genus Microsphaera, genus Microtetraspora, genus Microvirgula, genus Microbacterium, genus Microbulbifer, genus Microbispora, genus Micropruina, genus Micropolyspora, genus Micromonas, genus Micromonospora, genus Microlunatus, genus Mitsuokella, genus Megasphaera, genus Megamonas, genus Mesophilobacter, genus Mesoplasma, genus Mesorhizobium, genus Methanimicrococcus, genus Methanocalculus, genus Methanoculleus, genus Methanogenium, genus Methanocorpusculum, genus Methanococcoides, genus Methanococcus, genus Methanothermus, genus Methanothermobacter, genus Methanosaeta, genus Methanosarcina, genus Methanospirillum, genus Methanosphaera, genus Methanothrix, genus Methanobacterium, genus Methanohalobium, genus Methanohalophilus, genus Methanopyrus, genus Methanofollis, genus Methanoplanus, genus Methanobrevibacter. genus Methanomicrobium, genus Methanolacinia, genus Methanolobus, genus Methallosphaera, genus Methylarcula, genus Methylocaldum, genus Methylococcus, genus Methylcarcina, genus Methylocystis, genus Methylosinus, genus Methysphaera, genus Methylcella, genus Methylbacter, genus Methylbacterium, genus Methylobacillus, genus Methylopila, genus Methylophaga, genus Methylpholus, genus Methylovorus, genus Methylmicrobium, genus Methylomonas, genus Methylorhabdus, genus Meniscus, genus Melittangium, genus Melissococcus, genus Moellerella, genus Moorella, genus Mogibacterium, genus Modestobacter, genus Mobiluncus, genus Moraxella, genus Morganella, genus Mortiella, genus Morococcus, genus Eubacterium, genus Iodobacter, genus Yokenella, genus Rahnella, genus Raoultella, genus Lactococcus, genus Lactosphaera, genus Lactobacillus, genus Lachnospira, genus *Rathayibacter*, genus *Rhabdochromatium*, genus *Labrys*, genus *Ralstonia*, genus *Rarobacter*, genus *Lamprocystis*, genus *Lamprobacter*, genus *Lampropedia*, genus *Riemerella*, genus *Rickettsia*, genus *Rickettsiela*, genus *Rikenella*, genus *Listeria*, genus *Listonella*, genus *Lysobacter*, genus *Rhizobacter*, genus *Rhizobium*, genus *Rhizomonas*, genus *Lyticum*, genus *Limnobacter*, genus *Lewinella*, genus *Ruegeria*, genus *Rugamonas*, genus *Lucibacterium*, genus *Luteimonas*, genus *Luteococcus*, genus *Runella*, genus *Rubrivivax*, genus *Rubrimonas*, genus *Rubrobacter*, genus *Ruminococcus*, genus *Ruminobacter*, genus *Leifsonia*, genus *Leclercia*, genus *Lechevalieria*, genus *Legionella*, genus *Renibacterium*, genus *Levinea*, genus *Leptospira*, genus *Leptospirillum*, genus *Leptothrix*, genus *Leptotrichia*, genus *Leptonema*, genus *Leminorella*, genus *Lentzea*, genus *Leucothrix*, genus *Leuconostoc*, genus *Leucobacter*, genus *Lawsonia*, genus *Lautropia*, genus *Lochalimaea*, genus *Roseateles*, genus *Roseinatronobacter*, genus *Roseibium*, genus *Roseivivax*, genus *Roseococcus*, genus *Roseospira*, genus *Roseospirillum*, genus *Roseobacter*, genus *Roseovarius*, genus *Roseomonase*, genus *Roseburia*, genus *Rhodanobacter*, genus *Rothia*, genus *Rhodococcus*, genus *Rhodothermus*, genus *Rhodocyclus*, genus *Rhodocista*, genus *Rhodopseudomonas*, genus *Rhodospira*, genus *Rhodospirillum*, genus *Rhodothalassium*, genus *Rhodobaca*, genus *Rhodobacter*, genus *Rhodobium*, genus *Rhodovibrio*, genus *Rhodopila*, genus *Rhodoferax*, genus *Rhodoplanes*, genus *Rhodovulum*, genus *Rhodomicrobium*, genus *Lonepinella*, genus *Weissella*, genus *Waddlia* and the like.

Those which can also be exemplified are eukaryotic microorganisms such as genus *Issatchenkia*, *Candida*, genus *Cryptococcus*, genus *Kluyverintces*, genus *Kloeckera*, genus *Saccharomycodes*, genus *Saccharomyces*, genus *Zygosaccharomyces*, genus *Shizosaccharomyces*, genus *Sirobasidium*, genus *Strigmatomyces*, genus *Sporidobolus*, genus *Sporobolomyces*, genus *Dekkera*, genus *Debaryomyces*, genus *Trichosporon*, genus *Trigonopsis*, genus *Torulaspora*, genus *Tremella*, genus *Nadsonia*, genus *Nematospora*, genus *Hanseniaspora*, genus *Pichia*, genus *Fibulobasidium*, genus *Filobasidium*, genus *Filobasidiella*, genus *Bullera*, genus *Brettanomyces*, genus *Holtermannia*, genus *Malassezia*, genus *Metschnikowia*, genus *Lipomyces*, genus *Leucosporidium*, genus *Rhodosporidium*, genus *Rhodotorula*, genus *Acaulopage*, genus *Aquamortierella*, genus *Asellaria*, genus *Amoebidium*, genus *Amoeophilus*, genus *Arundinula*, genus *Utharomyces*, genus *Echinosporangium*, genus *Enterobryus*, genus *Endogone*, genus *Entomophthora*, genus *Kickxella*, genus *Genistellospora*, genus *Choanephora*, genus *Coemansia*, genus *Cochlonema*, genus *Conidiobolus*, genus *Saksenaea*, genus *Thamnidium*, genus *Thamnocephalis*, genus *Dispira*, genus *Dimargaris*, genus *Syncephalastrum*, genus *Syncephalis*, genus *Zoopage*, genus *Sclerocystis*, genus *Smittium*, genus *Basidiobolus*, genus *Parataeniella*, genus *Paramoebidium*, genus *Palavascia*, genus *Harpella*, genus *Piptocephalis*, genus *Pilobolus*, genus *Phycomyces*, genus *Blakeslea*, genus *Hesseltinella*, genus *Helicocephalum*, genus *Mycotypha*, genus *Radiomyces*, genus *Legeriomyces*, genus *Rhopalomyces*, genus *Acrasis*, genus *Acytostelium*, genus *Arcyria*, genus *Echinostelium*, genus *Echinosteliopsis*, genus *Oligonema*, genus *Cavostelium*, genus *Guttulinopsis*, genus *Clastoderma*, genus *Cribraria*, genus *Coenonia*, genus *Copromyxa*, genus *Comatricha*, genus *Colloderma*, genus *Dianema*, genus *Dictyostelium*, genus *Didymium*, genus *Diderma*, genus *Stemonitis*, genus *Thraustochytrium*, genus *Ceratiomyxa*, genus *Ceratiomyxella*, genus *Trichia*, genus *Physarum*, genus *Plasmodiophrora*, genus *Fuligo*, genus *Bursulla*, genus *Prorostelium*, genus *Protosporangium*, genus *Hemitrichia*, genus *Perichaena*, genus *Polysphondylium*, genus *Polymyxa*, genus *Labyrinthula*, genus *Lamproderma*, genus *Lycogala*, genus *Licea*, genus *Wardmyces*, genus *Actinopelte*, genus *Asterosporium*, genus *Arthrinium*, genus *Alternaria*, genus *Oidium*, genus *Clabosporium*, genus *Cladobotryum*, genus *Graphium*, genus *Colletotrichum*, genus *Sclerotium*, genus *Stagonospora*, genus *Stibella*, genus *Tubercularia*, genus *Bactridium*, genus *Pycnothrium*, genus *Phaeoisaria*, genus *Pestalozziella*, genus *Rhizoctonia*, genus *Rhinocladiella*, genus *Leptothyrium*, genus *Achlyogeton*, genus *Anisolpidium*, genus *Albugo*, genus *Ectrogella*, genus *Olipidium*, genus *Olpidiopsis*, genus *Catenaria*, genus *Chytridium*, genus *Cladochytrium*, genus *Coelomomyces*, genus *Gonapodya*, genus *Saprolegnia*, genus *Sirolpidium*, genus *Synchytrium*, genus *Haliphthoros*, genus *Harpochytrium*, genus *Pythium*, genus *Hyphochytrium*, genus *Physoderma*, genus *Phlyctidium*, genus *Blastocladia*, genus *Peronospora*, genus *Peronophythora*, genus *Micormycopsis*, genus *Megachytrium*, genus *Monoblepharis*, genus *Lagenidium*, genus *Rhizidiomyces*, genus *Rhizidium*, genus *Rhipidium*, genus *Leptomitus*, genus *Leptolegniella*, genus *Acremonium*, genus *Aspergillus*, genus *Absidia*, genus *Arachniotus*, genus *Arthrobotrys*, genus *Ulocladium*, genus *Echinobotryum*, genus *Exophiala*, genus *Epicoccum*, genus *Oidiodendron*, genus *Oedocephalum*, genus *Aureobasidium*, genus *Curvularia*, genus *Candelabrella*, genus *Cunninghamella*, genus *Gymnoascus*, genus *Cladosporium*, genus *Graphium*, genus *Gliocladium*, genus *Chrysosporium*, genus *Chromelosporium*, genus *Geotrichum*, genus *Geomyces*, genus *Chaetomium*, genus *Geniculifera*, genus *Gonatobotrysm*, genus *Coniothyrium*, genus *Circinella*, genus *Zygorhynchus*, genus *Diplodia*, genus *Cylindrocarpon*, genus *Scopulariopsis*, genus *Stachybotrys*, genus *Stemphylium*, genus *Sporothrix*, genus *Sepedonium*, genus *Dactylella*, genus *Talaromyces*, genus *Dratomyces*, genus *Trichurus*, genus *Trichocladium*, genus *Trichothecium*, genus *Trichoderma*, genus *Trichophyton*, genus *Nigrospora*, genus *Verticicladiella*, genus *Verticillium*, genus *Paecilomyces*, genus *Pithomyces*, genus *Bipolaris*, genus *Pyrenochaeta*, genus *Phialocephala*, genus *Phialophora*, genus *Phoma*, genus *Fusarium*, genus *Pestalotiopsis*, genus *Penicillium*, genus *Botrytis*, genus *Microsporum*, genus *Myrothecium*, genus *Mucor*, genus *Memnoniella*, genus *Monacrosporium*, genus *Monilia*, genus *Mortierella*, genus *Eupenicillium*, genus *Eurotium*, genus *Rhizopus*, genus *Leptographium*, genus *Robillarda*, genus *Austroboletus*, genus *Auricularia*, genus *Auriscalpium*, genus *Agaricus*, genus *Agrocybe*, genus *Asterophona*, genus *Astraeus*, genus *Aseroe*, genus *Anellaria*, genus *Amauroderma*, genus *Amanita*, genus *Armillaria*, genus *Armillariella*, genus *Alcuria*, genus *Ischnoderma*, genus *Inocybe*, genus *Inonotus*, genus *Ileodictyon*, genus *Wynnea*, genus *Verpa*, genus *Volvariella*, genus *Urnula*, genus *Echinodontium*, genus *Exidia*, genus *Elfvingia*, genus *Oudemansiella*, genus *Omphalina*, genus *Onnia*, genus *Catathelasma*, genus *Ganoderma*, genus *Camarophyllus*, genus *Chalciporus*, genus *Galerina*, genus *Calocera*, genus *Calostoma*, genus *Cantharellus*, genus *Cantharellula*, genus *Cyathus*, genus *Cyclomyces*, genus *Cystoderma*, genus *Cyptotrama*, genus *Cymatoderma*, genus *Gymnopilus*, genus *Kuehneromyces*, genus *Gyrodon*, genus *Gyroporus*, genus *Gyromitra*, genus *Guepinia*, genus *Xanthoconium*, genus *Xylaria*, genus *Xerocomus*, genus *Xeromphalina*, genus *Cudonia*, genus *Clavatia*, genus *Clavaria*, genus *Clavariadelphus*, genus *Clavicorona*, genus *Clavulina*, genus *Clavulinopsis*, genus *Craterellus*, genus *Clathrus*, genus *Clitocybe*, genus *Clitopilus*, genus *Crinipellis*, genus *Grifola*, genus *Cryptoderma*, genus *Cryptoporus*, genus *Crucibulum*, genus *Creolophus*, genus *Crepidotus*, genus *Chroogomphus*, genus *Chlorosplenium*, genus *Geastrum*, genus *Geolossum*, genus *Cotylidia*, genus *Conocybe*, genus *Kobayashia*, genus *Coprinus*, genus *Gomphidius*, genus *Gomphus*, genus *Coriolus*, genus *Cordyceps*, genus *Cortinarius*, genus *Coltricia*, genus *Collybia*, genus *Sarcoscypha*, genus *Sarcodon*, genus *Sarcodontia*, genus *Suillus*, genus *Schizophyllum*, genus *Squamanita*, genus *Scutellinia*, genus *Scleroderma*, genus *Stereum*, genus *Strobilomyces*, genus *Stropharia*, genus *Spathularia*, genus *Sparassis*, genus *Daedaleopsis*, genus *Dacryomyces*, genus *Daldinia*, genus *Dictyophora*, genus *Tylopilus*, genus *Tyromyces*, genus *Descolea*, genus *Thelephora*, genus *Tuloatoma*, genus *Trametes*, genus *Trichoglossum*, genus *Torichocoma*, genus *Tricoloma*, genus *Tricholomopsis*, genus *Tremella*, genus *Tremellodon*, genus *Naematoloma*, genus *Nidula*, genus *Neobulgaria*, genus *Baeospora*, genus *Paxillus*, genus *Battarea*, genus *Panaeolus*, genus *Panus*, genus *Panellus*, genus *Bankera*, genus *Hygrocybe*, genus *Hygrophorus*, genus *Hygrophoropsis*, genus *Bisporella*, genus *Pisolithus*, genus *Hydnum*, genus *Hydnellum*, genus *Hypsizygus*, genus *Piptoporus*, genus *Hypoxylon*, genus *Hymenochaete*, genus *Hirschioporus*, genus *Pyrrhoderma*, genus *Favolus*, genus *Phaeolus*, genus *Phaeolepiota*, genus *Phallus*, genus *Fistulina*, genus *Phyllotopsis*, genus *Phylloporus*, genus *Filoboletus*, genus *Phellinus*, genus *Fomitopsis*, genus *Fomes*, genus *Pholiota*, genus *Psathyrella*, genus *Psilocybe*, genus *Pseudocolus*, genus *Pseudohiatula*, genus *Prerula*, genus *Flammulina*, genus *Pulveroboletus*, genus *Bulgaria*, genus *Pluteus*, genus *Pleurocybella*, genus *Pleurotus*, genus *Plectania*, genus *Phlogiotis*, genus *Peziza*, genus *Penicilliopsis*, genus *Hebeloma*, genus *Hericium*, genus *Helvella*, genus *Podostroma*, genus *Polyozellus*, genus *Polyporus*, genus *Polyporellus*, genus *Holtermannia*, genus *Boibitius*, genus *Porphyrellus*, genus *Boletinus*, genus *Boletellus*, genus *Boletus*, genus *Boletopsis*, genus *Porodisculus*, genus *Bondarzewia*, genus *Macrocystidia*, genus *Macropodia*, genus *Macrolepiota*, genus *Marasmius*, genus *Marasmiellus*, genus *Microporus*, genus *Mycena*, genus *Mitrula*, genus *Mutinus*, genus *Melanoleuca*, genus *Merulius*, genus *Morchella*, genus *Laetiporus*, genus *Lactarius*, genus *Lasiosphaera*, genus *Laccaria*, genus *Ramaria*, genus *Lampteromyces*, genus *Lyophyllum*, genus *Rigidoporus*, genus *Lycoperdon*, genus *Rhizina*, genus *Lysurus*, genus *Limacella*, genus *Linder*, genus *Russula*, genus *Leucocoprinus*, genus *Leucopaxillus*, genus *Leotia*, genus *Resupinatus*, genus *Leccinum*, genus *Lepiota*, genus *Lepista*, genus *Lenzites*, genus *Lentaria*, genus *Lentinus*, genus *Lentinula*, genus *Lentinellus*, genus *Rozites*, genus *Rhodocybe*, genus *Rhodotus*, genus *Rhodophyllus* and the like.

A microorganism listed above which has an ability of producing an inventive coenzyme-binding glucose dehydrogenase has been deposited under its accession number to IFO, ATCC and the like, and can be obtained from known distributors and corporations. Such a microorganism may for example be a eukaryotic microorganism, more preferably mycotic microorganism. It is also possible to use the microorganism which is designated as "97508" and was deposited under FERM BP-08578 to International Patent Organism Depositary of National Institute of Advanced Industrial Science and Technology.

In one embodiment of the method for producing the inventive coenzyme-binding glucose dehydrogenase, a microorganism having an ability of producing the inventive coenzyme-binding glucose dehydrogenase is cultured in a nutrition medium, in which the coenzyme-binding glucose dehydrogenase is allowed to be produced and accumulated, and then recovered to yield a protein which is the coenzyme-binding glucose dehydrogenase and its salt.

The deposited inventive strain FERM BP-08578, a coenzyme-binding glucose dehydrogenase derived therefrom, and a method for obtaining the enzyme are described below.

1. Physicochemical Characteristics of FERM BP-08578-Derived Enzyme (1) Effect: On the basis of the classification by International Union of Biochemistry (IUB), the inventive enzyme corresponds to EC1.1.99.10, and catalyzes the reaction shown below which oxidizes a hydroxyl group in the 1st-position of glucose in the presence of an electron acceptor to yield glucono-δ-lactone.

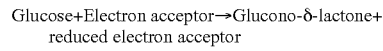

Glucose+Electron acceptor→Glucono-δ-lactone+ reduced electron acceptor

In the invention, the electron acceptor may for example be phenazine methosulfate, 1-methoxy-5-methylphenazinium methyl sulfate, 2,6-dichlorophenolindophenol, ferricyanides and the like.

(2) Substrate specificity: The relative reactivity (substrate specificity) of the inventive enzyme when using D-glucose and other substrates (all at the final concentration of 333 mM except for D-cellobiose at 193 mM, D-trehalose and D-raffinose at 121 mM) by the activity measurement method 1 described below are shown in Table 1. The relative reactivity (substrate specificity) when using D-glucose and maltose at the final concentrations of 550 mM and 100 mM are shown in Table 2. A higher activity was observed on D-glucose, while lower activity were observed on D-mannose, 1,5-anhydro-D-glucitol, D-cellobiose, D-trehalose, maltose, D-galactose, D-glucose-6-phosphate and D-fructose. Almost no activity was observed on L-arabinose, lactose, D-sorbitol, gluconic acid, sucrose, D-mannitol, L-sorbose, D-ribose, L-rhamnose, D-glucose-1-phosphate, D-raffinose, ethanol or glycerol.

(3) Optimum pH: pH7.0 to pH9.0.
(4) pH for stability: pH4.5 to pH8.5.
(5) Optimum temperature: Approximately 55° C.
(6) Thermal stability: Stable at 50° C. or below.
(7) Molecular weight: About 130 kDa when measured by a gel filtration method, and about 85 kDa when measured by a sodium dodecyl sulfate-polyacrylamide gel electrophoresis.
(8) Km value: 49.7 mM (D-glucose).
(9) Isoelectric point: The isoelectric point (pI) of the coenzyme-binding glucose dehydrogenase measured by an isoelectric focusing was about 4.4.
(10) Inhibitor: When each additive was added at 1 mM as a final concentration to the activity measurement method 1 described below and the activity was measured, an inhibitory effect of each additive was observed when comparing with the control group as shown in Table 3. When adding 1,10-phenanthroline (dissolved in methanol) at each final concentration to the activity measurement method 1 described below, the inhibitory effect shown in Table 4 was observed. The activity of this enzyme was inhibited potently by heavy metal ions (Ag+, $Cu^{2+}$, $Hg^{2+}$), and inhibited by 60% or higher by 1,10-phenanthroline, proflavin and $Mn^{2+}$.
(11) Coenzyme: Flavin adenine dinucleotide.

The amino acid sequence of the coenzyme-binding glucose dehydrogenase and the base sequence of a gene encoding it are also encompassed by the invention.

For producing the inventive coenzyme-binding glucose dehydrogenase, a microorganism for producing the coenzyme-binding glucose dehydrogenase may be any microorganism as far as it can produce the inventive coenzyme-binding glucose dehydrogenase, and the enzyme can efficiently be produced by using a microorganism, preferably a eukaryotic microorganism, more preferably a mycotic microorganism. It is especially preferred to use the microorganism which is designated as "97508" and was deposited under FERM BP-08578 to International Patent Organism Depositary of National Institute of Advanced Industrial Science and Technology AIST Tsukuba Central 6. 1-1. Higashi 1-Chome Tsukuba-shi Ibaraki-ken 305-8566 Japan. The deposited strain was isolated from a soil by Applicants, and has the mycological characteristics as described below. In the invention, any variant of the strain mentioned above may also be employed. Such a variant can be obtained for example by the irradiation with an ultraviolet light or X-ray or the treatment with a chemical modifier (NTG and the like).

2. Mycological Characteristics of FERM BP-08578

(1) Morphological characteristics: The morphological profile of the present strain when observed by an optical microscope after allowed to grow on a potato dextrose agar medium is described below. Each mycelium has a width of 2 μm to 4 μm, and has a regular septum. Most of the mycelia grow linearly, and have branches with almost no swollen mycelia being observed. Several mycelia are gathered together to form a mycclial bundle. The mycelial width is almost constant. The surface of a mycelium is smooth and the septum is slightly thick. A crystalloid is formed around the root of the aerial mycelia. No clamp connection is formed. The mycotic body formed in 2-week culture exhibited no formation of any sexual or asexual reproductive organs, and no oidia or thick-walled spores are present.

(2) Growth condition in various culture media: On all agar plates, each mycelium is in a form of a fluff. The aerial mycelium shade is white. On the potato dextrose agar plate, the backside color is pale orange to orange. The growth magnitude is medium, and a colony after culturing at 25° C. for 1 week has a diameter of 30 mm to 35 mm on the potato dextrose and oatmeal agar plate, and 37 mm to 38 mm on the malt extract agar plate. The production of soluble pigments of a pale yellow color on the potato dextrose agar plate and a slightly reddish to grey-reddish color on the oatmeal agar plate was noted. The mycotic body formed in 2-week culture exhibited no formation of reproductive organs such as a conidiophore, and no exudate was produced.

(3) Physiological characteristics: The present strain is an aerobic one and has an optimum growth temperature of about 37° C. on the potato dextrose agar plate.

3. Taxonomical Characteristics of FERM BP-08578

Based on the characteristics described above, the deposited strain "97508" was characterized with referring to Ainsworth & Bisby's Dictionary of the Fungi, 7th edition (Ed. by Hawksworth, Sutton, Ainsworth). As a result of this characterization, the deposited strain was revealed to be a microorganism classified into the genus *Aspergillus*. Then its genome sequence was subjected to BLAST homology search. An 18S rDNA fragment was amplified using a genome DNA as a template by PCR method, and then sequence of the purified PCR product was analyzed. In order to search for an analogous base sequence through GenBank (GenBank/EMBL/DDBJ international DNA sequence database), BLAST (Altschul et al., 1997) homology search was conducted, and revealed that this deposited strain "97508" is *Aspergillus terreus*.

In one embodiment of the method for producing a coenzyme-binding glucose dehydrogenase according to the invention, the microorganism described above is cultured to allow the coenzyme-binding glucose dehydrogenase to be expressed or produced by the microorganism in internal and/or external of its fungus body.

For the culture of the microorganism in the invention, any ordinary culture medium for microorganism may be used. Such medium may include a synthetic or natural medium, as long as it contains suitable amounts of carbon sources, nitrogen sources, inorganic substances and other trace elements required by the microorganism. The carbon sources may be glucose, sucrose, dextrin, starch, glycerin, syrup and the like. The nitrogen sources may be inorganic salts such as ammonium chloride, ammonium nitrate, ammonium sulfate and ammonium phosphate, amino acids such as DL-alanine and L-glutamic acid, as well as nitrogen-containing natural materials such as peptone, meat extract, yeast extract, malt extract, corn steep liquor and the like. The inorganic materials may for example be monosodium phosphate, disodium phosphate, monopottasium phosphate, dipotassium phosphate, magnesium sulfate, ferric chloride and the like.

The culture in order to obtain the inventive coenzyme-binding glucose dehydrogenase is conducted preferably in an aerobic condition for example by a shaking or aerating culture at a temperature of 25° C. to 60° C. at a pH of 5 to 8. The culture period ranges preferably from 2 days to 4 days. As a result of, such a culture, the coenzyme-binding glucose dehydrogenase can be produced and accumulated in the culture, especially in a culture fluid. By using this culture method, the coenzyme-binding glucose dehydrogenase can be produced by the microorganism and accumulated also internal fungus body. Subsequently, the coenzyme-binding glucose dehydrogenase can be recovered from the culture by means of an ordinary protein purification method. Such a method may be a method comprising incubating the microorganism followed by removing the microorganism for example by a centrifugation to obtain a supernatant, or a method comprising incubating the microorganism, recovering the cultured microorganism from the culture fluid by a centrifugation, crushing the cultured microorganism by a suitable method, and then isolating a supernatant for example by a centrifugation from the pelletized microorganism fluid. The coenzyme-binding glucose dehydrogenase contained in such a supernatant can be purified by a combination of suitable purification procedures such as salting out, solvent sedimentation, dialysis, ion exchange chromatography, hydrophobic adsorption chromatography, gel filtration, affinity chromatography, electrophoresis and the like.

In the culture for obtaining the inventive coenzyme-binding glucose dehydrogenase, a solid medium can be also used. The method for such a culture is not limited particularly, and may for example be a static culture, or a dynamic culture involving a continuous agitation of the culture, such as a rotational culture or fluidized bed culture, with a static culture being preferred due to a less expensive investment in equipment. Thereafter, as a method of obtaining the coenzyme-binding glucose dehydrogenase from the culture, an ordinary protein purification method can be adopted. That is, the culture is combined with water or other extraction medium and shaken, made free of any solid components such as bran by means of a centrifugation or filtration, thereby yielding an extract. It is also possible that the coenzyme-binding glucose dehydrogenase accumulated in the fungus bodies can be recovered by grinding the culture residue after obtaining the extract described above together with a an abrasive compound such as a sea sand, followed by adding water to extract the coenzyme-binding glucose dehydrogenase released from the fungus bodies. In order to obtain the entire coenzyme-binding glucose dehydrogenase, the entire culture is ground with an abrasive compound such as a sea sand, followed by adding water to extract both of the coenzyme-binding glucose dehydrogenase released from the fungus bodies and the coenzyme-binding glucose dehydrogenase secreted into the culture all at once. The coenzyme-binding glucose dehydrogenase contained in such a supernatant can be purified by a combination of suitable purification procedures such as salting out, solvent sedimentation, dialysis, ion-exchange chromatography, hydrophobic adsorption chromatography, gel filtration, affinity chromatography, electrophoresis and the like.

Alternatively, the inventive coenzyme-binding glucose dehydrogenase may also be a synthetic coenzyme-binding glucose dehydrogenase or a recombinant coenzyme-binding glucose dehydrogenase obtained by a gene engineering technology. Those skilled in the art can obtain the coenzyme-binding glucose dehydrogenase readily based on the disclosure of the protein or its salt derived from the physicochemical characteristics of the inventive coenzyme-binding glucose dehydrogenase. For example, the coenzyme-binding glucose dehydrogenase can be extracted from a microorganism including a fungi or a naturally occurring material such as an animal or plant, or can be obtained synthetically with referring to the amino acid sequence or the base sequence of the gene encoding it. Moreover, it is also possible to produce the coenzyme-binding glucose dehydrogenase industrially using a gene engineering method in which a gene segment of the coenzyme-binding glucose dehydrogenase gene is inserted into a known expression vector such as a commercial expression vector and then the resultant plasmid is used to transform a host such as *Escherichia coli* to obtain a transformant which is then cultured to obtain a target coenzyme-binding glucose dehydrogenase.

For measuring the activity of the inventive enzyme, the enzyme is diluted appropriately to a final concentration of 0.1 to 1 unit/ml. The enzymatic activity unit of the enzyme is the enzymatic activity enabling the oxidation of 1 μmol glucose per minute. The enzymatic activity of the inventive coenzyme-binding glucose dehydrogenase can be measured by the method shown below.

(i) Enzymatic Activity Measurement Method 1

To a 3-ml quartz cell (light path length: 1 cm), 1.0 ml of 0.1M potassium phosphate buffer (pH7.0), 1.0 ml of 1.0M D-glucose, 0.1 ml of 3 mM 2,6-dichlorophenolindophenol (hereinafter referred to as DCIP), 0.2 ml of 3 mM 1-methoxy-5-methylphenazinium methyl sulfate and 0.65 ml of water are added, which is followed by setting in a thermostat cell holder-mounted spectrophotometer and incubated at 37° C. for 5 minutes and then supplemented with 0.05 ml of the enzyme solution, and then measuring the change in the absorption of DCIP at 600 nm (ΔABS/min). Based on a molar extinction coefficient of DCIP at pH7.0 being regarded as $16.3 \times 10^3$ cm$^{-1}$M$^{-1}$ and the enzymatic activity corresponding to the reduction of 1 μmol of DCIP per minute being equivalent to 1 unit of the enzymatic activity, the enzymatic activity was determined from the change in the absorption on the basis of the following equation.

Enzymatic activity (unit/ml)=(−Δ*ABS*/16.3)×(3.0/0.05)×Enzyme dilution rate (ii) Enzymatic Activity Measurement Method 2

It was carried out that 3.4 μl of 1.0M potassium phosphate buffer (pH7.0), 0.1 ml of 1.0M D-glucose and 86.6 μl of 20 mM DCIP were incubated at 37° C. for 5 minutes, supplemented with 0.01 ml of an enzyme solution, stirred, reacted for 5 minutes, incubated at 100° C. for 3 minutes to quench the reaction. Thereafter, 0.19 ml of 100 mM glycine-sodium buffer (pH13.0), 0.01 ml of 2.0N potassium hydroxide were added, incubated at 37° C. for 10 minutes to convert D-gluconic acid in the solution into D-glucono-δ-lactone, and thereafter combined with 0.39 ml of a 100 mM Tris-HCl buffer (pH7.5) and 0.01 ml of 1.0N hydrochloric acid to achieve a neutral pH. The D-gluconic acid in the solution was quantified using the D-gluconic acid/D-glucono-δ-lactone measurement kit (Boehringer Mannheim). Since the enzymatic activity corresponding to the production of 1 μmol of D-glucono-δ-lactone per minute is equivalent substantially to 1 unit of this enzyme, this enzymatic activity was determined based on the amount of D-glucono-δ-lactone produced.

The invention relates to a material production and an analytical application employing an inventive coenzyme-binding glucose dehydrogenase, and also relates to the use in the modification of pharmaceutical or food product materials. In one example, the use is made in a method for eliminating glucose in a sample containing a biological material using the coenzyme-binding glucose dehydrogenase as a reagent, a measurement method as well as in such a reagent or a reagent composition. The use is made also in a method for producing an organic compound using the inventive coenzyme-binding glucose dehydrogenase as well as in a basic ingredient therefor.

The inventive coenzyme-binding glucose dehydrogenase is the enzyme that catalyzes a reaction for oxidizing glucose in the presence of an electron acceptor. In the invention, the reaction mentioned above employs the inventive coenzyme-binding glucose dehydrogenase. Such a coenzyme-binding glucose dehydrogenase is not limited particularly, and is preferably a coenzyme-binding glucose dehydrogenase derived from a eukaryotic microorganism producing the coenzyme-binding glucose dehydrogenase, with a coenzyme-binding glucose dehydrogenase derived from a mycotic microorganism being preferred especially.

Now the description is made with regard to the application of the coenzyme-binding glucose dehydrogenase obtained according to the invention. Since the coenzyme-binding glucose dehydrogenase is the enzyme that catalyzes a reaction for oxidizing glucose in the presence of an electron acceptor, any application in which the change resulting from such a reaction can be utilized can be mentioned. For example, the coenzyme-binding glucose dehydrogenase can be used in a reagent for measuring or eliminating glucose in a sample containing a biological material. It is also possible to use in medical and clinical fields, and also in the material production and analysis employing the coenzyme-binding glucose dehydrogenase.

The inventive biosensor may be any sensor having a reaction layer containing the inventive coenzyme-binding glucose dehydrogenase as an enzyme. For example, the biosensor can be produced in a method wherein an enzymatic reaction layer formed thereon containing a hydrophilic polymer, a redox enzyme and an electron acceptor is brought into contact with an electrode system consisting of an action electrode, a counter electrode and a reference electrode is formed for example by a screen printing on an insulating board. When a substrate-containing sample solution is dropped onto the enzymatic reaction layer in this biosensor, the enzymatic reaction layer is dissolved to effect the reaction between the enzyme and the substrate, thereby reducing the electron acceptor. After completion of the enzymatic reaction, the reduced electron acceptor is oxidized electrochemically, whereupon the biosensor can measure the concentration of the substrate in the sample based on the resultant oxidation current value. Otherwise, a biosensor can be constructed so that the chromogenic intensity or pH change is detected. By using above mentioned biosensors, any of various materials can be measured by selecting the enzyme whose substrate is the target substance. For example, when the inventive coenzyme-binding glucose dehydrogenase is selected as an enzyme, a glucose sensor enabling the measurement of the concentration of glucose in a sample solution can be produced.

As the electron acceptor in the biosensor, a chemical substance having an excellent ability of transferring an electron can be employed. Such a chemical substance having an excellent ability of transferring an electron is generally a substance referred to as "electron carrier", "mediator" or "oxidation/reduction(redox)-mediating agent", such as the electron transfer and the redox-mediating agent listed in JP-W-2002-526759.

In the biosensor, an inexpensive potassium ferricyanide (potassium hexacyanoferrate (III)) is generally employed as an electron acceptor, and usually used at a final concentration of 1 mM or less. Nevertheless, the inventive coenzyme-binding glucose dehydrogenase enables a more sensitive measurement of D-glucose when using potassium ferricyanide at a concentration as high as 2 to 500 mM, more preferably 30 to 100 mM. A preferred embodiment of the inventive measurement method, measurement reagent, measurement compound, biosensor and the like is characterized by the use of potassium ferricyanide in its relevant measurement system at a final concentration of 2 to 500 mM.

EXAMPLES

The present invention is further described in the following Examples, by which the invention is not restricted without departing from its scope. In the following Examples, the quantification of a coenzyme-binding glucose dehydrogenase was conducted as described above.

Example 1

Culture of Deposited Strain 97508

100 ml of a culture medium (pH6.0) containing 1% glucose (WAKO PURE CHEMICAL), 2% defatted soybean (NIPPON SHOKUHAN), 0.5% of corn steep liquor (KYODO SHOJI) and 0.1% magnesium sulfate (Nacalai Tesque) was placed in a 500-ml culture flask, which was sterilized at 121° C. for 20 minutes, cooled, inoculated with a platinum loop of the deposited strain 97508, shaken at 30° C. for 88 hours to obtain a seed culture of the strain. 4 L of the culture medium having the composition similar to that described above but supplemented with an antifoam agent was added to a 5-L jar fermenter, which was sterilized at 121° C. for 30 minutes, cooled, inoculated with 40 ml of the seed culture described above, cultured at 28° C. for 31 hours with aerating and shaking to obtain a preliminary culture of the strain. Then, 160 L of the culture medium having the composition similar to that described above but supplemented with an antifoam agent was added to a 200-L jar fermenter, which was sterilized at 121° C. for 20 minutes, cooled, inoculated with 1.6 L of the preliminary culture described above, cultured at 28° C. for 41 hours with aerating and shaking. After completion of the culture, the culture fluid was centrifuged to obtain the supernatant.

Example 2

Isolation of Coenzyme-Binding Glucose Dehydrogenase from the Culture Supernatant By the following Steps 2.1 to 2.5, the coenzyme-binding glucose dehydrogenase was isolated.

2.1 Concentration

160 L of the culture supernatant of Example 1 was concentrated through an ultrafiltration membrane "Pellicon 2 Module" (Millipore), and transferred into a 20 mM potassium phosphate buffer (pH7.5) to obtain a crude enzyme solution.

2.2 Purification by Butyl-TOYOPEARL 650M (TOSOH) (First Process)

The abovementioned crude enzyme solution was prepared in 65%-saturated ammonium sulfate (pH7.5), and centrifuged to obtain a supernatant. This treated crude enzyme solution was loaded onto a Butyl-TOYOPEARL 650M column (diameter: 4.7 cm, height: 7.7 cm) which had previously been equilibrated with a 20 mM potassium phosphate buffer (pH7.5) containing 65% ammonium sulfate; and thereby allowing the enzyme is absorbed therein. This column was washed with the same buffer solution, and then the enzyme was allowed to be eluted with 20 mM potassium phosphate buffer (pH7.5) containing 30% ammonium sulfate to collect an active fraction. The enzyme was further eluted by a gradient elution starting from the same buffer to 20 mM potassium phosphate buffer (pH7.5), and pooled with the former active fraction.

2.3. Purification by DEAE-CELLULOFINE A-500 (SEIKAGAKU KOGYO)

The abovementioned active fraction was concentrated through an ultrafiltration membrane "Pellicon 2 Module", desalted, and equilibrated with a 15 mM Tris-HCl buffer (pH8.5). This fraction was loaded onto a DEAE-CELLULOFINE A-500 column (diameter: 4.7 cm, height: 5.2 cm) which had previously been equilibrated with the same buffer solution, and the eluate was collected.

2.4 Purification by Butyl-TOYOPEARL 650M (TOSOH) (Second Process)

The abovementioned eluate was prepared in 65%-saturated ammonium sulfate (pH7.5), and centrifuged to obtain a supernatant. This supernatant was loaded onto a Butyl-TOYOPEARL 650M column (diameter: 4.7 cm, height: 3.6 cm) which had previously been equilibrated with a 20 mM potassium phosphate buffer (pH7.5) containing 65% ammonium sulfate; thereby allowing the enzyme is absorbed. This column was washed with the same buffer solution, and then the enzyme was allowed to be eluted with 20 mM potassium phosphate buffer (pH7.5) containing 30% ammonium sulfate to collect an active fraction.

2.5 Purification by TSKgel G3000SW (TOSOH)

The abovementioned active fraction was concentrated through a pencil type membrane concentration module "ACP-0013" (ASAHI KASEI), desalted, and equilibrated with 50 mM potassium phosphate buffer (pH5.5) containing 0.2M sodium chloride. This fraction was loaded onto a TSKgel G3000SW (diameter: 2.15 cm, height: 60 cm) which had previously been equilibrated with the buffer described above, and the enzyme was eluted with the same buffer to obtain an active fraction. The active fraction was concentrated through a centriplus 10 (Amicon), desalted, and transferred into a 50 mM citric acid-sodium phosphate buffer (pH5.5). The resultant enzyme approximately had a specific activity of 1,100 unit/mg, and a purification degree of about 170 times greater than that of the crude enzyme solution.

Example 3

Test of Characteristics of Coenzyme-Binding Glucose Dehydrogenase

The coenzyme-binding glucose dehydrogenase isolated in Example 2 described above was examined for its effect, optimum pH, pH for stability, optimum temperature, thermal stability, substrate specificity, molecular weight, inhibitor and coenzyme.

3.1 Effect

The coenzyme-binding glucose dehydrogenase was reacted with 500 mM D-glucose in the presence of 8.66 mM DCIP, and the reaction product was quantified using D-gluconic acid/D-glucono-δ-lactone measurement kit. As a result, the production of D-gluconic acid was identified, and it was revealed that the inventive coenzyme-binding glucose dehydrogenase is the enzyme that catalyzes a reaction for oxidizing a hydroxyl group in the 1-position of D-glucose.

3.2 Optimum pH

The buffer solution according to the Enzymatic activity measurement method 2 was replaced with the citric acid-sodium phosphate buffer (pH4.0 to 5.5), potassium phosphate buffer (pH6.5 to 7.5), Tris-HCl buffer (pH8.0 to 9.0) or glycine-sodium hydroxide buffer (pH9.5 to 10.0) (each 17 mM as a final concentration), and the enzymatic activity of the purified enzyme was measured at various pH ranges similarly to Enzymatic activity measurement method 2 (FIG. 1). As a result, the optimum pH of the coenzyme-binding glucose dehydrogenase was 7.0 to 9.0.

3.3 pH for Stability

Figure 2:
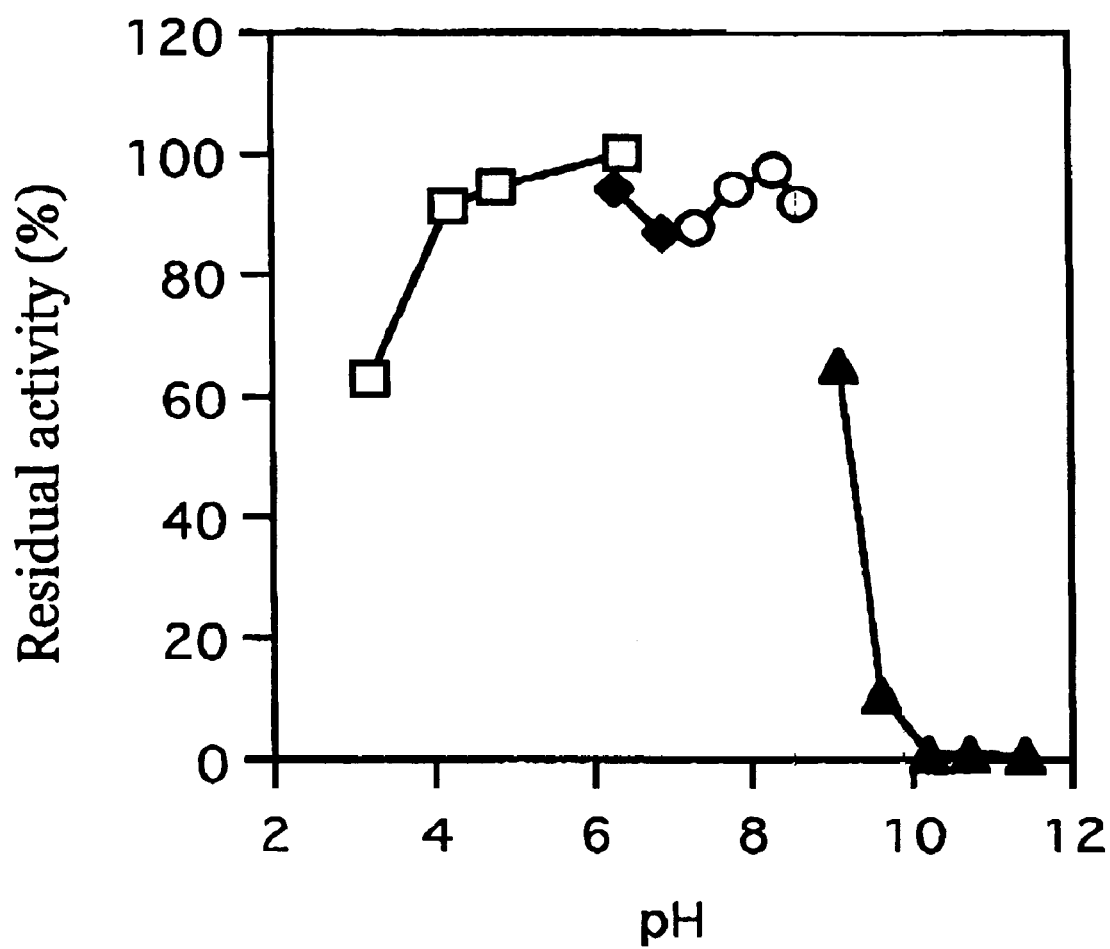
FIG. 2 shows a graph representing the relationship between the residual activity (%) of the coenzyme-binding glucose dehydrogenase and the pH, in Example 3 (3.3). Symbols show measured values and types of buffer solutions, which are □: citric acid-sodium phosphate buffer (pH3.2 to 6.4), ♦: potassium phosphate buffer (pH6.3 to 6.9), ○: Tris-HCl buffer (pH7.3 to 8.6) and ▲: glycine-sodium hydroxide (pH9.1 to 11.4). The stable pH of the enzyme was 4.5 to 8.5.

The coenzyme-binding glucose dehydrogenase was dissolved in each 50 mM buffer, i.e., citric acid-sodium phosphate buffer (pH3.2 to 6.4), potassium phosphate buffer (pH6.3 to 6.9), Tris-HCl buffer (pH7.3 to 8.6) or glycine-sodium hydroxide buffer (pH9.1 to 11.4) and kept at 40° C. for 60 minutes, and then the enzymatic activity was examined by the method according to the activity measurement method 1, and a ratio of residual enzymatic activity was analyzed (FIG. 2). As a result, the pH for the stability of the coenzyme-binding glucose dehydrogenase was pH4.5 to 8.5.

3.4 Optimum Temperature

Figure 3:
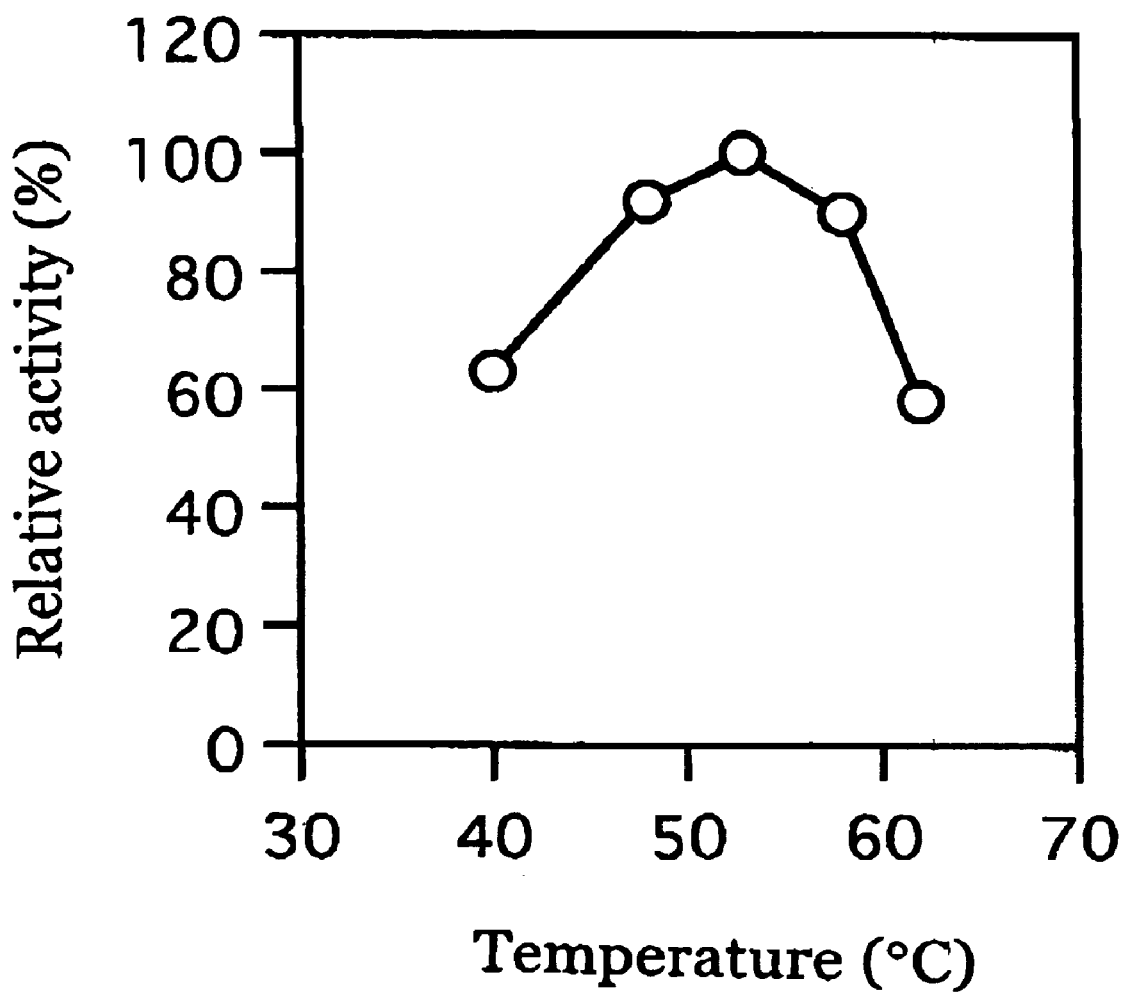
FIG. 3 shows a graph representing the relationship between the relative activity (%) of the coenzyme-binding glucose dehydrogenase and the temperature, in Example, 3 (3.4). The optimum temperature of the enzyme was approximately 55° C.

The coenzyme-binding glucose dehydrogenase was dissolved in 50 mM citric acid-sodium phosphate buffer (pH5.5) and examined for the enzymatic activity over the range from 30° C. to 62° C. by the Enzymatic activity measurement method 1 described above (FIG. 3). As a result, the optimum temperature of the coenzyme-binding glucose dehydrogenase was about 55° C.

3.5 Thermal Stability

Figure 4:
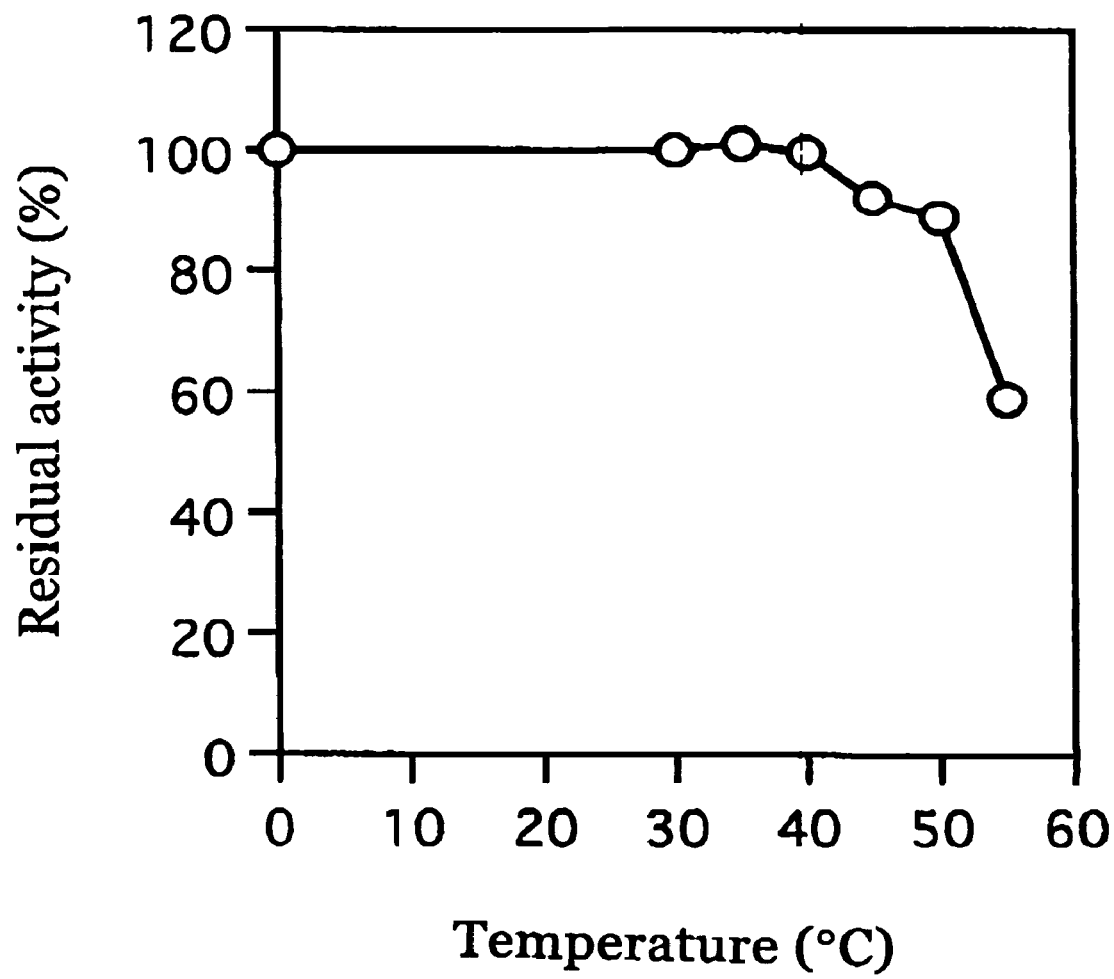
FIG. 4 shows a graph representing the relationship between the residual activity (%) of the coenzyme-binding glucose dehydrogenase in Example 3 (3.5) and the treatment temperature. The enzyme was revealed to be stable at 50° C. or below.

The coenzyme-binding glucose dehydrogenase was dissolved in 50 mM citric acid-sodium phosphate buffer (pH5.5), kept at several points of the temperature ranging from 0° C. to 55° C. for 15 minutes, and then examined for the enzymatic activity by the Enzymatic activity measurement method 1, and the ratio (%) of residual enzymatic activity was analyzed (FIG. 4). The ratio (%) of residual enzymatic activity was calculated with regarding the enzymatic activity after keeping at 0° C. for 15 minutes as 100%. As a result, the coenzyme-binding glucose dehydrogenase kept its enzymatic activity at a level as high as 89% even at 50° C., showing the stability at about 50° C. or below.

3.6 Substrate Specificity and Km Value

Employing each of D-glucose and other substrates (each at 333 mM as a final concentration, except for D-cellobiose at 193 mM, D-trehalose and D-raffinose at 121 mM), the enzymatic activity of this enzyme was measured by the Enzymatic activity measurement method 1. The activity on each substrate is represented as a relative value to the activity of this enzyme on D-glucose being regarded as 100%, and shown in Table 1.

Similarly, the relative reactivities (enzymatic activity) on D-glucose and maltose each at two final concentrations, i.e. 550 mM and 100 mM, were measured. The results are represented as relative values based on the value on D-glucose.

As evident from these results, the coenzyme-binding glucose dehydrogenase acts potently on D-glucose, and weakly on D-mannose, 1,5-anhydro-D-glucitol, D-cellobiose, D-trehalose, maltose, D-galactose, D-glucose-6-phosphate and D-fructose. This enzyme exhibited almost no effect on L-arabinose, lactose, D-sorbitol, gluconic acid, sucrose, D-mannitol, L-sorbose, D-ribose, L-rhamnose, D-glucose-1-phosphate, D-raffinose, ethanol or glycerol. The Km value of this enzyme was 49.7 mM on D-glucose.

TABLE 1

| Substrate | Relative activity (%) |
| --- | --- |
| D-Glucose | 100 |
| 2-Deoxy-D-glucose | 48 |
| D-Xylose | 9.1 |
| D-Mannose | 2.8 |
| 1,5-Anhydro-D-glucitol | 2 |
| D-Cellobiose | 2 |
| D-Trehalose | 1.7 |
| Maltose | 1.4 |
| D-Galactose | 1.2 |
| D-Glucose-6-phosphate | 1.1 |
| D-Fructose | 0.86 |
| L-Arabinose | 0.1> |
| Lactose | 0.1> |
| D-Sorbitol | 0.1> |
| Gluconic acid | 0.1> |
| Sucrose | 0.1> |
| D-Mannitol | 0.1> |
| L-Sorbose | 0.1> |
| D-Ribose | 0.1> |
| L-Rhamnose | 0.1> |
| D-Glucose-1-phosphate | 0.1> |
| D-Raffinose | 0.1> |
| Ethanol | 0.1> |
| Glycerol | 0.1> |

TABLE 2

| Substrate | Final Conc.(mM) | Relative activity (%) |
| --- | --- | --- |
| D-Glucose | 550 | 100 |
| Maltose | 550 | 2.8 |
| D-Glucose | 100 | 100 |
| Maltose | 100 | 0.5 |

3.7 Molecular Weight and Subunit Molecular Weight

The coenzyme-binding glucose dehydrogenase was dissolved in a 50 mM potassium phosphate buffer (pH7.5) containing 0.2M NaCl, and analyzed on a TSKgel-G3000SW (diameter: 0.75 cm, length: 60 cm, TOSOH) using the same buffer solution as a mobile phase. When using a molecular weight marker (Oriental Yeast) as an index, the molecular weight of the coenzyme-binding glucose dehydrogenase was revealed to be about 130 kDa. Using a 12.5% polyacrylamide gel, the inventive coenzyme-binding glucose dehydrogenase was subjected to an SDS-polyacrylamide gel electrophoresis (SDS-PAGE) according to the method by Laemmli et al (Nature, (1970) 227:680-685). After the running, the gel was stained with Coomassie brilliant blue, and the mobility was compared with that of the molecular weight marker (Amersham Pharmacia Biotech), which revealed that the subunit molecular weight of the inventive coenzyme-binding glucose dehydrogenase was about 85 kDa.

3.8 Inhibitor

Each of the various additives shown in Table 3 was added as an inhibitor at 1 mM as a final concentration to the reaction system of the Enzymatic activity measurement method 1, and the activity of the coenzyme-binding glucose dehydrogenase was measured by the Enzymatic activity measurement method 1. In a control group, the procedure similar to that of Enzymatic activity measurement method 1 was conducted except for adding no additives shown in Table 3. Based on the enzymatic activity observed in the control group being regarded as 100%, the activity in the presence of each additive was calculated as a relative activity, the difference of which from the control group activity was regarded as a % inhibitory effect. As a result, the inhibitory effect shown in Table 3 was observed.

On the other hand, in the Enzymatic activity measurement method 1 described above, 1,10-phenanthroline respectively dissolved in methanol at 1 mM, 5 mM, 1 mM, 25 mM and 50 mM as final concentrations was added, and the activity of the inventive coenzyme-binding glucose dehydrogenase was measured in accordance with the Enzymatic activity measurement method 1. The final concentration of methanol relative to each reaction system was 10% (v/v). In a control group, methanol was added in the Enzymatic activity measurement method 1 at 10% (v/v) as a final concentration. The results are shown in Table 4. It was revealed that the inhibitory effect of 1,10-phenanthroline was as high as 62.0% at 1 mM, 76% at 5 mM, 85% at 10 mM, 91% at 25 mM and 95% at 50 mM as final concentrations of 1,10-phenanthroline.

The inhibitory effect on the inventive coenzyme-binding glucose dehydrogenase varied depending on the type of the additive, and was the highest in the presence of heavy metal ion (such ad $Ag^+$, $Cu^{2+}$ and $Hg^{2+}$), and was 60% or more in the presence of 1,10-phenanthroline, proflavin and $Mn^{2+}$.

TABLE 3

| Additive | Inhibition (%) |
| --- | --- |
| None | 0 |
| $NaN_3$ | 0 |
| $ZnCl_2$ | 0 |
| $AlCl_3$ | 0 |
| Benzoic acid | 0 |
| EDTA | 0.4 |
| $CdCl_2$ | 0.8 |
| LiCl | 0.9 |
| Aminoguanidine sulfate | 1.1 |
| $H_2O_2$ | 1.7 |
| N-Ethylmaleimide | 1.8 |
| Urea | 1.9 |
| NaCl | 2.5 |
| Tirone | 2.5 |
| $BaCl_2$ | 2.6 |
| $PbCl_2$ | 2.7 |
| $MgCl_2$ | 2.8 |
| Fumaric acid | 3.4 |
| Cycloserine | 3.6 |
| DL-Penicillamine | 4.3 |

TABLE 3-continued

| Additive | Inhibition (%) |
| --- | --- |
| Meso-tartaric acid | 5.6 |
| Citric acid | 5.6 |
| $CaCl_2$ | 5.7 |
| Quinacrine | 5.0 |
| TritonX-100 | 6.2 |
| $CoCl_2$ | 7.0 |
| Malic acid | 8.1 |
| D-Tartaric acid | 8.5 |
| Iodoacetic acid | 9.5 |
| Cysteamine | 9.8 |
| 2,2'-Bipyridine | 10.8 |
| 8-Quinolinol | 13.9 |
| KCN | 14.5 |
| $NiCl_2$ | 16.5 |
| $FeCl_3$ | 25.0 |
| Maleic acid | 26.2 |
| Acrinol | 29.0 |
| 2-Nitrobenzoic acid | 44.3 |
| $SnCl_2$ | 45.5 |
| Acriflavine | 49.0 |
| 1,10-Phenanthroline | 62.0 |
| Proflavin | 62.0 |
| $MnCl_2$ | 75.5 |
| $AgNO_3$ | 99.4 |
| $CuCl_2$ | 100 |
| $HgCl_2$ | 100 |

TABLE 4

| Final concentration of 1,10-phenanthroline (mM) | Inhibit (%) |
| --- | --- |
| 0 | 0 |
| 50 | 95 |
| 25 | 91 |
| 10 | 85 |
| 5 | 76 |

3.9. Coenzyme

The inventive coenzyme-binding glucose dehydrogenase solution was supplemented with D-glucose and subjected to the absorption analysis, which indicated the disappearance of the maximum absorptions observed at 385 nm and 465 nm in response to the supplement, revealing that the coenzyme was flavin adenine dinucleotide. These maximum absorptions are specific to FAD, and it was not observed in a control group reaction system constructed by excluding FAD only.

Example 4

Glucose Quantification

Figure 5:
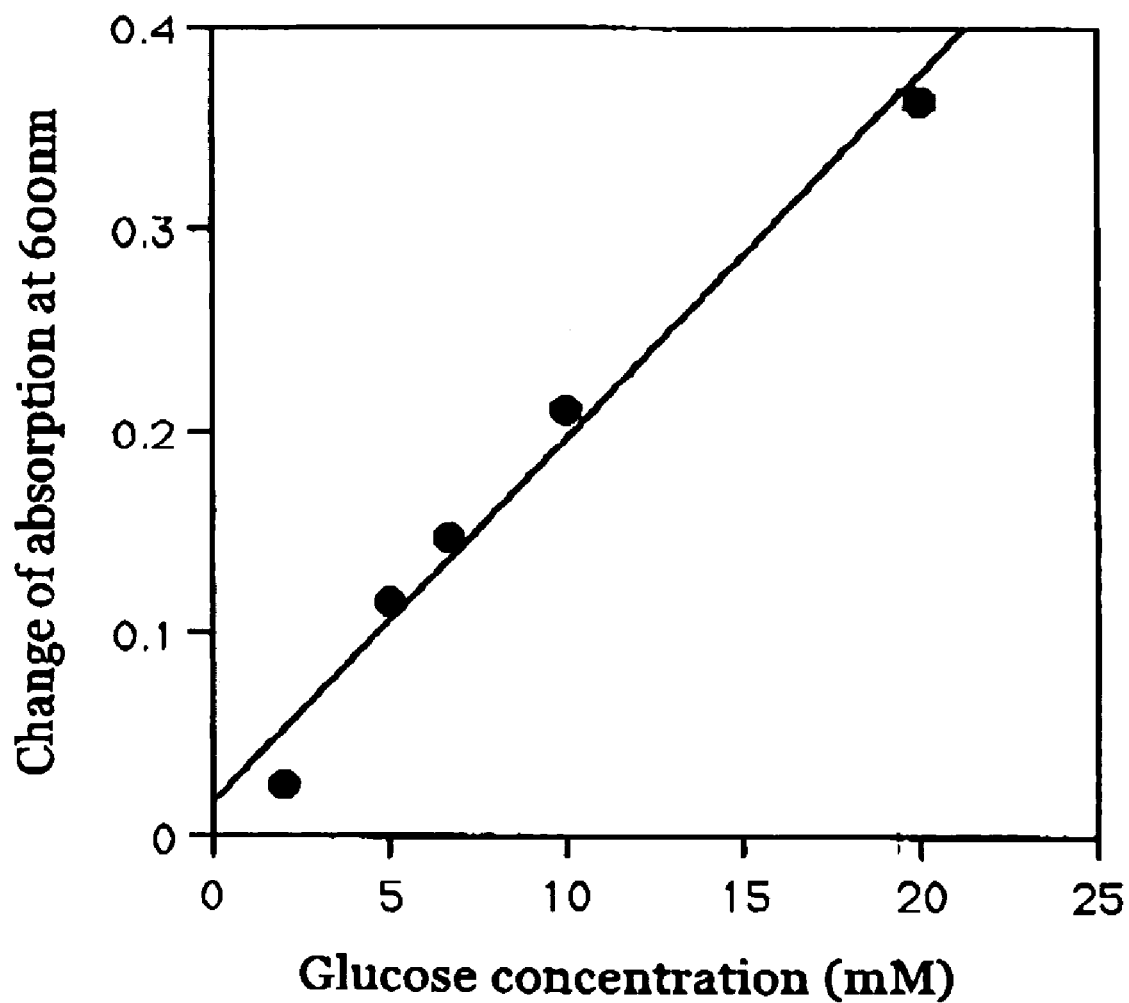
FIG. 5 shows a calibration curve for quantifying the glucose in Example 4, which indicates the change in DCIP absorption vs the glucose level.

The coenzyme-binding glucose dehydrogenase derived from the deposited strain 97508 purified in Example 2 described above was employed, and the absorption reduction rate was measured using D-glucose at the concentration ranging from 0.333 to 33 mM instead of 333 mM D-glucose in the Enzymatic activity measurement method 1. Thus, the transition in the absorption was measured at each D-glucose concentration of 0.333 mM, 0.5 mM, 1 mM, 2 mM, 5 mM, 6.67 mM, 10 mM, 20 mM and 33 mM. The results of the measurement are shown in FIG. 5.

As a result, a calibration curve (correlation coefficient r=0.997) was obtained; thereby, it was apparent that the quantification of D-glucose employing the coenzyme-binding glucose dehydrogenase is possible.

Example 5

Measurement of Glucose by Enzyme-Immobilizing Electrode

Figure 6:
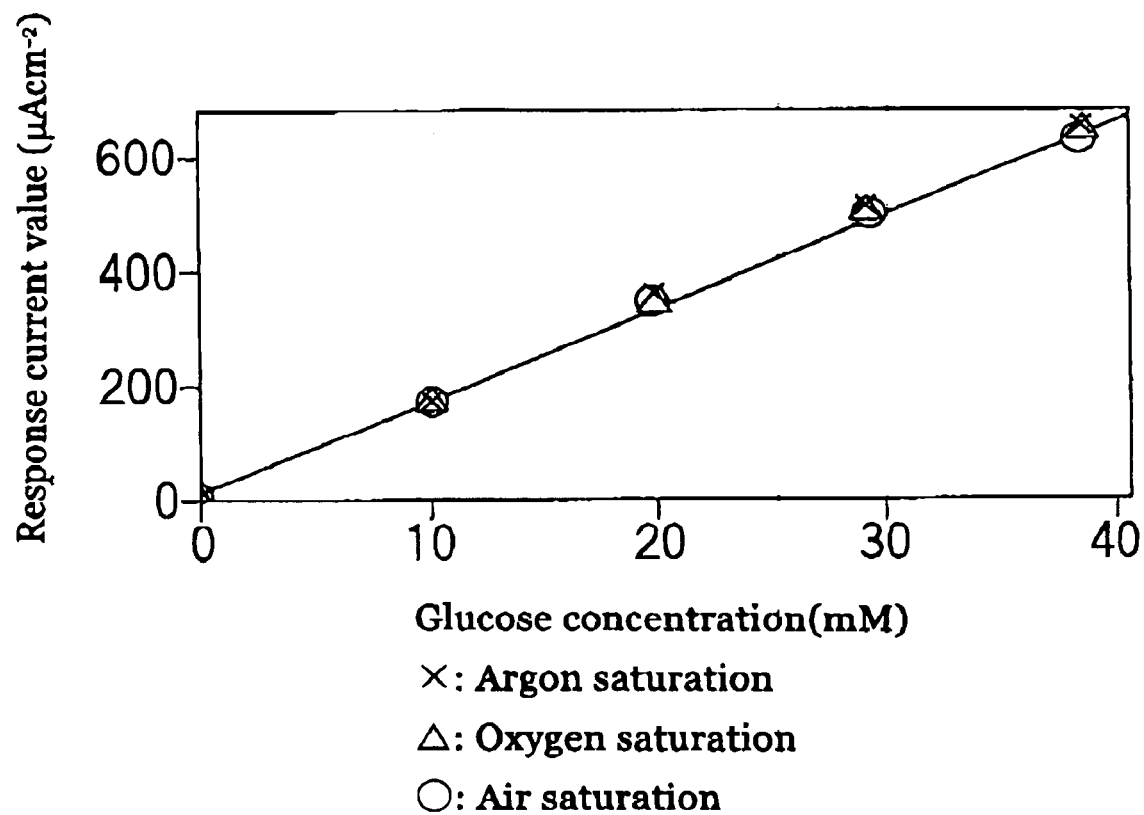
FIG. 6 shows a calibration curve for a glucose measurement using a coenzyme-binding glucose dehydrogenase-immobilizing electrode in Example 5. Symbols represent the conditions under: ×: argon saturation, Δ: oxygen saturation and ○: air saturation.

The coenzyme-binding glucose dehydrogenase derived from the deposited strain 97508 purified in Example 2 described above was employed to measure D-glucose by an enzyme-immobilizing electrode. A glassy carbon (GC) electrode on which 3.4 U of this enzyme was immobilized was employed to measure the response current to the glucose concentration. In an electrolytic cell, 2.7 ml of 100 mM sodium phosphate buffer (pH7.0) and 0.3 ml of 1M aqueous solution of potassium hexacyanoferrate (III) potassium ferricyanide) were added. The GC electrode was connected to the potentiostat BAS100B/W (BAS), and the solution was stirred at 40° C. in each condition of argon saturation, oxygen saturation and air saturation while applying +500 mV to the silver-silver chloride reference electrode. 30 µl of a 1M D-glucose solution was added to these systems, and the current value in the stationary phase was measured. The same amount of the 1M D-glucose solution was further added, and the current value was measured, these procedure being repeated each three times. The resultant current values vs the known glucose concentrations (about 10, 20, 30 and 40 mM) were plotted to obtain a calibration curve (FIG. 6). Thereby, it was apparent that the quantification of glucose by the enzyme-immobilizing electrode employing the coenzyme-binding glucose dehydrogenase is possible. It was also revealed, based on the consistent calibration curve obtained regardless of any gas saturated conditions, that the coenzyme-binding glucose dehydrogenase is extremely inert to the oxygen and that it is possible to quantify D-glucose by the enzyme-immobilizing electrode utilizing the enzyme without being subjected to any effect of the oxygen.

Example 6

Measurement of Glucose in Standard Serum by Enzyme-Immobilizing Electrode

Analogous to Example 5, the concentration of glucose in a serum was measured by the enzyme-immobilizing electrode using the control serum I WAKO B (WAKO PURE CHEMICAL). In an electrolytic cell, 2.4 ml of 100 mM sodium phosphate buffer (pH7.0) and 0.3 ml of 1M aqueous solution of potassium hexacyanoferrate (III) (potassium ferricyanide) were added, and the serum was added when the current value became stationary and the current value was measured. Similarly, the D-glucose solutions of known concentrations were measured to obtain a calibration curve. The glucose concentration in the serum was identified by the calibration curve method to be 4.5 mM, which was in agreement with the concentration of the glucose identified by the hexokinase-glucose-6-phosphate dehydrogenase method. Accordingly, it was revealed that the quantification of D-glucose in serum by the enzyme-immobilizing electrode employing the coenzyme-binding glucose dehydrogenase employed in the invention is possible.

INDUSTRIAL APPLICABILITY

According to the present invention, it became possible to provide a soluble coenzyme-binding glucose dehydrogenase whose activity on altose is 5% or less and which is inhibited by 1,10-phenanthroline. Furthermore, a method for producing the coenzyme-binding glucose dehydrogenase suitable to an industrial production and a microorganism producing therefor are also provided. As a result, it becomes possible to apply the coenzyme-binding glucose dehydrogenase to an industrial application, and more particularly, it becomes possible to measure the blood sugar level even in a diabetes patient receiving an infusion containing maltose. Also by using the inventive coenzyme-binding glucose dehydrogenase, a trace amount of the glucose can be measured even with a glucose sensor, thus enabling the utility. It also becomes possible to use in a material production or analysis including a method for measuring or eliminating glucose in a sample using the coenzyme-binding glucose dehydrogenase as well as a method for producing an organic compound, thereby providing a highly utilizable enzyme, which enables use for modifying a material in the fields of pharmaceuticals, clinical studies and food products.

The invention claimed is:

1. An isolated soluble flavin dependent glucose dehydrogenase obtainable from *Aspergillus terreus*, or a mutant thereof which results from a deletion, substitution or addition of one amino acid residue, which:
   (a) catalyzes a reaction for oxidizing glucose in the presence of an electron acceptor;
   (b) has a 5% or less specific activity to maltose relative to the enzymatic activity to glucose; and
   (c) is inhibited by 1,10-phenanthroline.

2. The flavin dependent glucose dehydrogenase of claim 1, wherein its activity is inhibited by 50% or more in the presence of a 1 mM final concentration of 1,10-phenanthroline.

3. The flavin dependent glucose dehydrogenase of claim 1, which oxidizes a hydroxyl group at the 1-position of glucose.

4. The flavin dependent glucose dehydrogenase or mutant thereof of claim 1, wherein the flavin compound-binding glucose dehydrogenase is obtainable from the *Aspergillus terreus* deposited under the accession number FERM BP-08578.

5. An isolated soluble flavin dependent glucose dehydrogenase obtainable from *Aspergillus terreus* having:
   (a) an optimum pH of pH 7.0 to pH 9.0;
   (b) a pH for stability of pH 4.5 to pH 8.5;
   (c) an optimum temperature of approximately 55° C.;
   (d) a thermal stability at 50° C. or below;
   (e) a molecular weight of about 130 kDa when measured by a gel filtration method, and about 85 kDa when measured by a sodium dodecyl sulfate-polyacrylamide gel electrophoresis;
   (f) a Km value of 49.7mM (D-glucose); and
   (g) an isoelectric point (pI) of the coenzyme-binding glucose dehydrogenase measured by an isoelectric focusing of about 4.4.

6. An isolated *Aspergillus terreus* which is capable of producing the flavin dependent glucose dehydrogenase of claim 1.

7. An isolated *Aspergillus terreus* as deposited under the Accession number FERM BP-08578.

* * * * *